United States Patent
Arai et al.

(10) Patent No.: US 9,921,201 B2
(45) Date of Patent: Mar. 20, 2018

(54) CALIBRATION CURVE CREATING METHOD AND CALIBRATION CURVE CREATION APPARATUS

(71) Applicant: SEIKO EPSON CORPORATION, Tokyo (JP)

(72) Inventors: Yoshifumi Arai, Matsumoto (JP); Hikaru Kurasawa, Fujimi-machi (JP)

(73) Assignee: SEIKO EPSON CORPORATION, Tokyo (JP)

( * ) Notice: Subject to any disclaimer, the term of this patent is extended or adjusted under 35 U.S.C. 154(b) by 484 days.

(21) Appl. No.: 14/334,022

(22) Filed: Jul. 17, 2014

(65) Prior Publication Data

US 2015/0025851 A1     Jan. 22, 2015

(30) Foreign Application Priority Data

Jul. 18, 2013 (JP) .................................. 2013-149736

(51) Int. Cl.
*G01N 33/48* (2006.01)
*G01N 33/00* (2006.01)
(Continued)

(52) U.S. Cl.
CPC ....... *G01N 33/0098* (2013.01); *G01N 21/274* (2013.01); *G01N 2021/8466* (2013.01); *G06F 19/00* (2013.01)

(58) Field of Classification Search
CPC .............. G01N 33/0098; G01N 21/27; G01N 2201/129; G01N 21/84; G01N 2021/8466; G01N 21/274
(Continued)

(56) References Cited

U.S. PATENT DOCUMENTS

2002/0038196 A1* 3/2002 Johnson ............. G01N 21/4788
702/179
2005/0149300 A1* 7/2005 Ruchti ............... A61B 5/14532
703/2
(Continued)

FOREIGN PATENT DOCUMENTS

| JP | A-2001-99710 | 4/2001 |
| JP | A-2007-44104 | 2/2007 |

(Continued)

OTHER PUBLICATIONS

Chen, Z. et al., "Extracting Chemical Information from Spectral Data with Multiplicative Light Scattering Effects by Optical Path-Length Estimation and Correction," Analytical Chemistry, Nov. 15, 2006, pp. 7674-7681, vol. 78, No. 22.

(Continued)

*Primary Examiner* — Stephanie Bloss
(74) *Attorney, Agent, or Firm* — Oliff PLC

(57) ABSTRACT

A calibration curve creating method includes: (a) acquiring observation data of a plurality of samples of a test object; (b) acquiring content of a target component of each sample; (c) estimating a plurality of independent components when the observation data of each sample is separated into the plurality of independent components, and acquiring a mixing coefficient corresponding to the target component for each sample; and (d) acquiring a regression equation of a calibration curve. (c) includes acquiring an independent component matrix by performing a first preprocessing including normalization of the observation data, a second preprocessing including whitening, and an independent component analysis process in this order. β divergence is used as an independence index of the independent component analysis process, and a robust regression method is used in (d).

8 Claims, 27 Drawing Sheets

(51) Int. Cl.
*G01N 21/27* (2006.01)
*G01N 21/84* (2006.01)
*G06F 19/00* (2018.01)

(58) Field of Classification Search
USPC .......................................... 702/19, 104, 189
See application file for complete search history.

(56) References Cited

U.S. PATENT DOCUMENTS

| | | | | |
|---|---|---|---|---|
| 2008/0034025 | A1* | 2/2008 | Zubkov | G01D 18/00 |
| | | | | 708/403 |
| 2013/0197816 | A1* | 8/2013 | Kurasawa | G01N 21/274 |
| | | | | 702/27 |
| 2014/0101083 | A1* | 4/2014 | Nicholson | G06N 99/005 |
| | | | | 706/12 |
| 2014/0122392 | A1* | 5/2014 | Nicholson | G06N 99/005 |
| | | | | 706/12 |
| 2014/0178348 | A1* | 6/2014 | Kelsey | C12Q 1/6886 |
| | | | | 424/93.71 |

FOREIGN PATENT DOCUMENTS

| | | |
|---|---|---|
| JP | 2009-204526 A | 9/2009 |
| JP | A-2013-36973 | 2/2013 |
| JP | A-2013-160574 | 8/2013 |
| JP | A-2013-160575 | 8/2013 |
| JP | A-2013-160576 | 8/2013 |

OTHER PUBLICATIONS

Hyvärinen, A. et al., Independent Component Analysis, Chapters 6 (Principal Component Analysis and Whitening) and 8 (ICA by Maximization of Nongaussianity), pp. 125-144 and 165-202.

Mihoko, M. et al., "Robust Blind Source Separation by β-Divergence," pp. 1-29, 2002.

Ikeda, S. et al., "Independent component analysis for noisy data," pp. 1-28.

Maronna, R. et al., Robust Statistics—Theory and Methods, Chapters 4 and 5 (Linear Regression 1 and 2), pp. 87-171 and Chapter 7 (Generalized Linear Models) pp. 229-246.

Toivianen, M. et al. "Blind Source Separation in Diffuse Reflectance NIR Spectroscopy Using Independent Component Analysis". Journal Chemometrics, p. 514-522, 2010.

* cited by examiner

|       | $Y_1$ | $Y_2$ | $\cdots$ | $Y_m$ |
|-------|-------|-------|----------|-------|
| $B_1$ | $\hat{a}_{11}$ | $\hat{a}_{12}$ | $\cdots$ | $\hat{a}_{1m}$ |
| $B_2$ | $\hat{a}_{21}$ | $\hat{a}_{22}$ | $\cdots$ | $\hat{a}_{2m}$ |
| $\vdots$ | $\vdots$ | $\vdots$ | $\cdots$ | $\vdots$ |
| $B_n$ | $\hat{a}_{n1}$ | $\hat{a}_{n2}$ | $\cdots$ | $\hat{a}_{nm}$ |

INDEPENDENT COMPONENT / SAMPLE NUMBER — TB

TARGET COMPONENT ORDER k = 2

FIG. 6

ANALYSIS RESULT OF MIXTURE OF SUCROSE AND SALT

| | PROCESS CONDITIONS 1 | PROCESS CONDITIONS 2 | PROCESS CONDITIONS 3 | PROCESS CONDITIONS 4 | PROCESS CONDITIONS 5 | PROCESS CONDITIONS 6 | PROCESS CONDITIONS 7 | PROCESS CONDITIONS 8 |
|---|---|---|---|---|---|---|---|---|
| PROCESS CONDITIONS / FIRST PREPROCESSING (NORMALIZATION) | SNV | SNV | PNS | SNV | PNS | PNS | SNV | PNS |
| SECOND PREPROCESSING (WHITENING) | PCA | FA | PCA | PCA | PCA | FA | FA | FA |
| INDEPENDENCE INDEX OF ICA | KURTOSIS | KURTOSIS | KURTOSIS | β DIVERGENCE | β DIVERGENCE | KURTOSIS | β DIVERGENCE | β DIVERGENCE |
| VARIATION FACTOR | — | — | — | — | — | — | — | — |
| $R^2$ | 0.850 | 0.855 | 0.962 | 0.851 | 0.942 | 0.908 | 0.856 | 0.951 |
| SEP | 8.964 | 8.838 | 7.363 | 8.929 | 6.896 | 8.875 | 8.798 | 6.005 |
| DRAWING | FIG. 12A | FIG. 12B | FIG. 12C | FIG. 12D | FIG. 12E | FIG. 12F | FIG. 12G | FIG. 12H |

MEASUREMENT DATA: 8 LEVELS BY DIVIDING INTO AMOUNT OF 10% OF MIXING RATIO OF 20% TO 90% OF MIXTURE OF SUCROSE AND SALT

CALIBRATION TARGET: RATIO (%) PER UNIT VOLUME OF SUCROSE

MEASUREMENT METHOD: MEASURE ABSORBANCE WITH SPECTROPHOTOMETER $R^2$: SQUARE OF CORRELATION COEFFICIENT

SEP: SQUARE-ROOT OF SUM OF SQUARES OF EXPECTED ERROR

FIG. 13

ANALYSIS RESULT OF (VOICE ITEMS v1 AND v2 + THREE TYPES OF VARIATION)

| | | PROCESS CONDITIONS 1 | PROCESS CONDITIONS 2 | PROCESS CONDITIONS 3 | PROCESS CONDITIONS 4 | PROCESS CONDITIONS 5 | PROCESS CONDITIONS 6 | PROCESS CONDITIONS 7 | PROCESS CONDITIONS 8 |
|---|---|---|---|---|---|---|---|---|---|
| PROCESS CONDITIONS | FIRST PREPROCESSING (NORMALIZATION) | (SNV) | (SNV) | PNS | (SNV) | PNS | PNS | (SNV) | PNS |
| | SECOND PREPROCESSING (WHITENING) | PCA | FA | PCA | PCA | PCA | FA | FA | FA |
| | INDEPENDENCE INDEX OF ICA | KURTOSIS | KURTOSIS | KURTOSIS | β DIVERGENCE | β DIVERGENCE | KURTOSIS | β DIVERGENCE | β DIVERGENCE |
| | VARIATION FACTOR | THREE TYPES | THREE TYPES | THREE TYPES | THREE TYPES | THREE TYPES | THREE TYPES | THREE TYPES | THREE TYPES |
| | $R^2$ | 0.533 | 0.620 | 0.589 | 0.585 | 0.945 | 0.957 | 0.806 | 0.986 |
| | SEP | 0.141 | 0.127 | 0.136 | 0.132 | 0.051 | 0.100 | 0.095 | 0.034 |
| | DRAWING | FIG. 14A | FIG. 14B | FIG. 14C | FIG. 14D | FIG. 14E | FIG. 14F | FIG. 14G | FIG. 14H |

MEASUREMENT DATA: D VOICE ITEMS v1 AND v2 IN RANDOM RATIO. CREATED 40 SAMPLES

CALIBRATION TARGET: RATIO OF VOICE ITEM v1

MEASUREMENT METHOD: SIMULATION

ADDITION OF VARIATION FACTOR: GAUSSIAN NOISE + SPIKE NOISE + BASELINE VARIATION
GAUSSIAN NOISE: GAUSSIAN NOISE HAVING DISPERSION OF 0.05
SPIKE NOISE: SPIKE NOISE ACCORDING TO $\chi^2$ DISTRIBUTION OF PARAMETER 5 IS MIXED AT RATIO OF 1%
BASELINE VARIATION: AVERAGE VALUE VARIATION, LINEAR VARIATION, AND QUADRATIC FUNCTION VARIATION ARE RANDOMLY ADDED IN ORDER OF $10^1$, $10^{-5}$, AND $10^{-6}$
BASELINE VARIATION = $10^{-1} \ast rand \ast E + 10^{-5} \ast rand \ast \lambda + 10^{-6} \ast rand \ast \lambda^2$ (rand IS PSEUDORANDOM NUMBER)

$R^2$: SQUARE OF CORRELATION COEFFICIENT

SEP: SQUARE-ROOT OF SUM OF SQUARES OF EXPECTED ERROR

FIG. 15

ANALYSIS RESULT OF (VOICE ITEMS v1 AND v2 + ONE TYPE OF VARIATION FACTOR)

| | | PROCESS CONDITIONS 1 | PROCESS CONDITIONS 2 | PROCESS CONDITIONS 1 | PROCESS CONDITIONS 3 | PROCESS CONDITIONS 1 | PROCESS CONDITIONS 4 |
|---|---|---|---|---|---|---|---|
| PROCESS CONDITIONS | FIRST PREPROCESSING (NORMALIZATION) | (SNV) | (SNV) | (SNV) | PNS | (SNV) | (SNV) |
| | SECOND PREPROCESSING (WHITENING) | PCA | FA | PCA | PCA | PCA | PCA |
| | INDEPENDENCE INDEX OF ICA | KURTOSIS | KURTOSIS | KURTOSIS | KURTOSIS | KURTOSIS | β DIVERGENCE |
| | VARIATION FACTOR | GAUSSIAN NOISE | GAUSSIAN NOISE | BASELINE VARIATION | BASELINE VARIATION | SPIKE NOISE | SPIKE NOISE |
| $R^2$ | | 0.967 | 0.996 | 0.828 | 1.000 | 0.681 | 0.997 |
| SEP | | 0.043 | 0.032 | 0.086 | 0.002 | 0.118 | 0.047 |
| DRAWING | | FIG. 16A | FIG. 16B | FIG. 16C | FIG. 16D | FIG. 16E | FIG. 16F |

MEASUREMENT DATA: MIXED VOICE ITEMS v1 AND v2 IN RANDOM RATIO. CREATED 40 SAMPLES

CALIBRATION TARGET: RATIO OF VOICE ITEM v1

MEASUREMENT METHOD: SIMULATION

ADDITION OF VARIATION FACTOR: ANY ONE OF GAUSSIAN NOISE, SPIKE NOISE, AND BASELINE VARIATION
    GAUSSIAN NOISE: GAUSSIAN NOISE HAVING DISPERSION OF 0.15
    SPIKE NOISE: SPIKE NOISE ACCORDING TO $\chi^2$ DISTRIBUTION OF PARAMETER 5 IS MIXED AT RATIO OF 1%
    BASELINE VARIATION: AVERAGE VALUE VARIATION, LINEAR VARIATION, AND QUADRATIC FUNCTION VARIATION ARE
    RANDOMLY ADDED IN ORDER OF $10^{-1}$, $10^{-5}$, AND $10^{-6}$
    BASELINE VARIATION = $10^{-1}*rand*E + 10^{-5}*rand*\lambda + 10^{-6}*rand*\lambda^2$ (rand IS PSEUDORANDOM NUMBER)

$R^2$: SQUARE OF CORRELATION COEFFICIENT

SEP: SQUARE-ROOT OF SUM OF SQUARES OF EXPECTED ERROR

FIG. 17

APPROXIMATION : $\hat{Y} = q_1 t_1 + q_2 t_2 + \cdots q_A t_A + e$ ... (a)

HEREIN $q = (T'T)^{-1} T' y$ ... (b)

$T = (t_1, t_2 \cdots t_A)$

CALIBRATION CURVE CREATING METHOD AND CALIBRATION CURVE CREATION APPARATUS

This application claims the benefit of Japanese Patent Application No. 2013-149736, filed on Jul. 18, 2013. The content of the aforementioned application is incorporated herein by reference in its entirety.

BACKGROUND

1. Technical Field

The present invention relates to a technology of creating a calibration curve used in acquiring content of a target component of a test object from observation data of the test object.

2. Related Art

In the related art, there is provided a method of performing independent component analysis of observation data of a test object which is obtained by observing at a plurality of different positions, setting an independent component calculated by the independent component analysis as a fundamental function, and representing the observation data as a linear sum of the fundamental function, to analyze concentration or the like of a target component (see JP-A-2007-44104).

However, in the technology of the related art, a plurality different of observation data items of the test object are necessary every time when performing calibration of a target component of the test object, and it is difficult to perform the calibration with high accuracy from one observation data item.

Various noise may be included in the observation data. In this case, accuracy of the independent component analysis or the calibration using that may be degraded.

Further, the observation data may vary depending on the test object, due to unevenness of a composition or a structure of the test object. In such a case, the accuracy of the independent component analysis or the calibration using that may also be degraded.

SUMMARY

An advantage of some aspects of the invention is to allow highly precise calibration of a test object from one observation data item, when performing calibration of a target component for the test object.

The invention can be implemented as the following forms or application examples.

Application Example 1

This application example is directed to a calibration curve creating method of creating a calibration curve used in acquiring content of a target component of a test object from observation data of the test object, the method including: (a) causing a computer to acquire the observation data of a plurality of samples of the test object; (b) causing the computer to acquire content of the target component of each sample; (c) causing the computer to estimate a plurality of independent components when the observation data of each sample is separated into the plurality of independent components, and to acquire a mixing coefficient corresponding to the target component for each sample based on the plurality of independent components; and (d) causing the computer to acquire a regression equation of the calibration curve based on the content of the target component of the plurality of samples and the mixing coefficient for each sample, in which (i) causing the computer to acquire an independent component matrix including the independent component of each sample, (ii) causing the computer to acquire an estimated mixing matrix showing a vector set for regulating a ratio of an independent component element of each independent component in each sample, from the independent component matrix, and (iii) causing the computer to acquire a correlation of content of the target component of the plurality of samples, for each vector included in the estimated mixing matrix, and to select the vector which is determined to have a highest correlation, as a mixing coefficient corresponding to the target component, are included in (c), in (i), the computer acquires the independent component matrix by performing a first preprocessing including normalization of the observation data, a second preprocessing including whitening, and an independent component analysis process in this order, the computer uses β divergence as an independence index of the independent component analysis process, and a robust regression method is used in (d) acquiring the regression equation of the calibration curve.

According to the calibration curve creating method of Application Example 1, a calibration curve for acquiring the amount of the target component included in the test object from the observation data of the test object is created from the observation data acquired from each sample and the content of the target component of the plurality of samples of the test object. Accordingly, it is possible to acquire the content of the target component with high accuracy by using this calibration curve, even when one observation data item of the test object is used. Therefore, if the calibration curve is previously created according to the calibration curve creating method of Application Example 1, it is only necessary to acquire one observation data item of the test object when performing calibration. As a result, it is possible to acquire a target component amount from one observation data item which is an actually-measured value, with high accuracy. In addition, the estimated mixing matrix is acquired and the vector having a high correlation with respect to the content of the target component of the sample is extracted from the estimated mixing matrix, and therefore it is possible to obtain a mixing coefficient having high estimation accuracy. Further, since the β divergence is used as the independence index of the independent component analysis process, it is possible to decrease an effect of an outlier such as spike noise included in an absorbance spectrum to improve calibration accuracy. Since the regression equation of the calibration curve is acquired by using the robust regression method, it is possible to decrease the effect of the outlier to improve calibration accuracy, even in a case where the outlier exists in the observation data.

Application Example 2

This application example is directed to the calibration curve creating method according to Application Example 1, wherein the computer performs normalization after a process performed by project on null space in the first preprocessing.

According to this method, since the process performed by the project on null space is performed in the first preprocessing, it is possible to decrease an effect of baseline variation included in the observation data to improve calibration accuracy.

Application Example 3

This application example is directed to the calibration curve creating method according to Application Example 1 or 2, wherein the computer performs whitening by factor analysis in the second preprocessing.

According to this method, since the whitening by the factor analysis is performed in the second preprocessing, it is possible to decrease an effect of noise (particularly, random noise) included in the observation data to improve calibration accuracy.

Application Example 4

This application example is directed to a calibration curve creation apparatus which creates a calibration curve used in acquiring content of a target component of a test object from observation data of the test object, the apparatus including: a sample observation data acquisition unit which acquires the observation data of a plurality of samples of the test object; a sample target component amount acquisition unit which acquires the content of the target component of each sample; a mixing coefficient estimation unit which estimates a plurality of independent components when the observation data of each sample is separated into the plurality of independent components, and acquires a mixing coefficient corresponding to the target component for each sample based on the plurality of independent components; and a regression equation calculation unit which acquires a regression equation of the calibration curve based on the content of the target component of the plurality of samples and the mixing coefficient for each sample, in which the mixing coefficient estimation unit includes an independent component matrix calculation unit which acquires an independent component matrix including each independent component of each sample, an estimated mixing matrix calculation unit which acquires an estimated mixing matrix showing a vector set for regulating a ratio of an independent component element of each independent component in each sample, from the independent component matrix, and a mixing coefficient selection unit which acquires a correlation of content of the target component of the plurality of samples, for each vector included in the estimated mixing matrix, and selects the vector which is determined to have a highest correlation, as a mixing coefficient corresponding to the target component, the independent component matrix calculation unit acquires the independent component matrix by performing a first preprocessing including normalization of the observation data, a second preprocessing including whitening, and an independent component analysis process in this order, the independent component matrix calculation unit uses $\beta$ divergence as an independence index of the independent component analysis process, and the regression equation calculation unit uses a robust regression method.

According to the calibration curve creation apparatus of Application Example 4, in the same manner as the calibration curve creating method according to Application Example 1, it is only necessary to acquire one observation data item of the test object when performing the calibration. Accordingly, it is possible to acquire the target component amount from one observation data item which is an actually-measured value, with high accuracy. In addition, since the $\beta$ divergence is used as the independence index of the independent component analysis process, it is possible to decrease an effect of an outlier such as spike noise included in the absorbance spectrum to improve calibration accuracy. Further, since the regression equation of the calibration curve is acquired by using the robust regression method, it is possible to decrease the effect of the outlier to improve calibration accuracy, even in a case where the outlier exists in the observation data.

Application Example 5

This application example is directed to the calibration curve creation apparatus according to Application Example 4, wherein the independent component matrix calculation unit performs normalization after a process performed by project on null space in the first preprocessing.

According to this apparatus, since the process performed by the project on null space is performed in the first preprocessing, it is possible to decrease an effect of baseline variation included in the observation data to improve calibration accuracy.

Application Example 6

This application example is directed to the calibration curve creation apparatus according to Application Example 4 or 5, wherein the independent component matrix calculation unit performs whitening by factor analysis in the second preprocessing.

According to this apparatus, since the whitening by the factor analysis is performed in the second preprocessing, it is possible to decrease an effect of noise (particularly, random noise) included in the observation data to improve calibration accuracy.

Application Example 7

This application example is directed to the calibration curve creation apparatus according to any one of Application Examples 4 to 6, which further includes a storage unit which stores the independent component matrix calculated by the independent component matrix calculation unit, a target component order which shows a position of the mixing coefficient selected by the mixing coefficient selection unit in the estimated mixing matrix, and the regression equation calculated by the regression equation calculation unit.

According to this configuration, in the calibration curve creation apparatus, it is possible to store the independent component matrix, the target component order, and the regression equation in the storage unit.

Further, the invention can be implemented as the following various aspects, and for example, can be implemented as an aspect of a computer program which implements the configuration of each unit included in the calibration curve creation apparatus as a function, an aspect of the computer program or a non-transitory storage medium in which the computer program is recorded, or the like.

BRIEF DESCRIPTION OF THE DRAWINGS

The invention will be described with reference to the accompanying drawings, wherein like numbers reference like elements.

FIG. 6 is an explanatory diagram for illustrating an estimated mixing matrix ^A.

FIG. 13 is a diagram showing comparison of calibration accuracy of FIG. 12A to FIG. 12H.

FIG. 15 is a diagram showing comparison of calibration accuracy of FIG. 14A to FIG. 14H.

FIG. 17 is a diagram showing comparison of calibration accuracy of FIG. 16A to FIG. 16F.

DESCRIPTION OF EXEMPLARY EMBODIMENTS

Hereinafter, embodiments of the invention will be described in the following order.

A. Calibration Curve Creating Method
B. Calibrating Method of Target Component
C. Various Algorithms and Effect Thereof on Calibration Accuracy
D. Effect of Robust Regression Method on Calibration Accuracy
E. Reason for Employing Robust Regression Method
F. Modification Examples The following terms will be used in the description of the embodiments of the invention.

ICA: Independent Component Analysis
SNV: Standard Normal Variate Transformation
PNS: Project on Null Space
PCA: Principal Components Analysis
FA: Factor Analysis Hereinafter, an embodiment of the invention will be described. A first embodiment of the invention relates to a method of creating a calibration curve for acquiring an amount of chlorophyll included in green vegetables from a spectrum of spectral reflectance of the green vegetables as the observation data. Examples of the green vegetables include spinach, Japanese mustard spinach, and green peppers.

A. CALIBRATION CURVE CREATING METHOD

Figure 1:
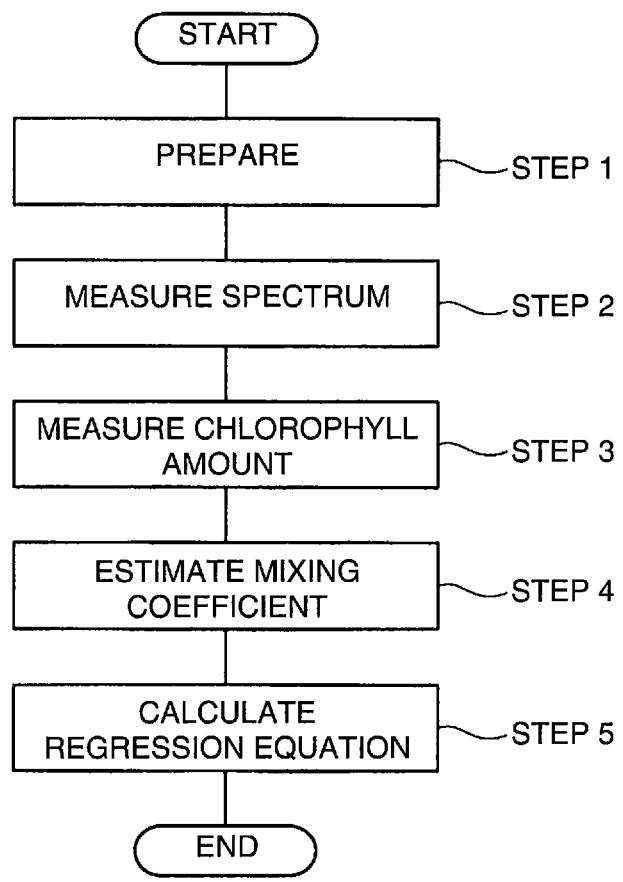
FIG. 1 is a flowchart showing a calibration curve creating method as a first embodiment of the invention.

FIG. 1 is a flowchart showing a calibration curve creating method as the first embodiment of the invention.

As shown in the drawing, the calibration curve creating method is configured with five steps from a step 1 to a step 5. The steps 1 to 5 are performed in this order. The steps 1 to 5 will be described in order.

Step 1

The step 1 is a preparation step and is performed by an operator. The operator prepares the plurality of green vegetables (for example, spinach) which are the same type as each other but have different freshness, as samples. n (n is an integer equal to or larger than 2) samples are used in the first embodiment.

Step 2

A step 2 is a measurement step of a spectrum, and is performed by the operator using a spectroscopic measurement instrument. The operator images each of the plurality of samples prepared in the step 1 with the spectroscopic measurement instrument, to measure the spectrum of the spectral reflectance for each sample. The spectroscopic measurement instrument is a well-known instrument which measures the spectrum by allowing light from an object to be measured to penetrate through a spectroscope and receiving a spectrum output from the spectroscope by an imaging surface of an imaging element. A relationship represented by the following formula (1) is satisfied between the spectrum of the spectral reflectance and the absorbance spectrum.

$$[\text{Absorbance}] = -\log_{10} [\text{Reflectance}] \quad (1)$$

The measured spectrum of the spectral reflectance is converted into the absorbance spectrum using the formula (1). The conversion into the absorbance is performed because it is necessary to satisfy linear combination in a mixed signal analyzed in independent component analysis which will be described later and the linear combination is satisfied for the absorbance from the Lambert-Beer law. Accordingly, in the step 2, the absorbance spectrum may be measured instead of the spectral reflectance spectrum. As a measured result, data of absorbance distribution showing a property of an object to be measured with respect to the wavelength is output. The data of the absorbance distribution is also referred to as spectral data.

Specifically, in the step 2, the operator images a predetermined portion of each sample to measure the spectrum of the predetermined portion. Herein, the predetermined portion may be any portion as long as it is a portion in each sample, but is preferably a portion which does not have significantly different freshness from the freshness of the entire sample. For example, in a case where freshness of a certain portion is extremely decreased in one sample, a portion not including the portion with the decreased freshness is set as the predetermined portion to be measured.

Figure 2:
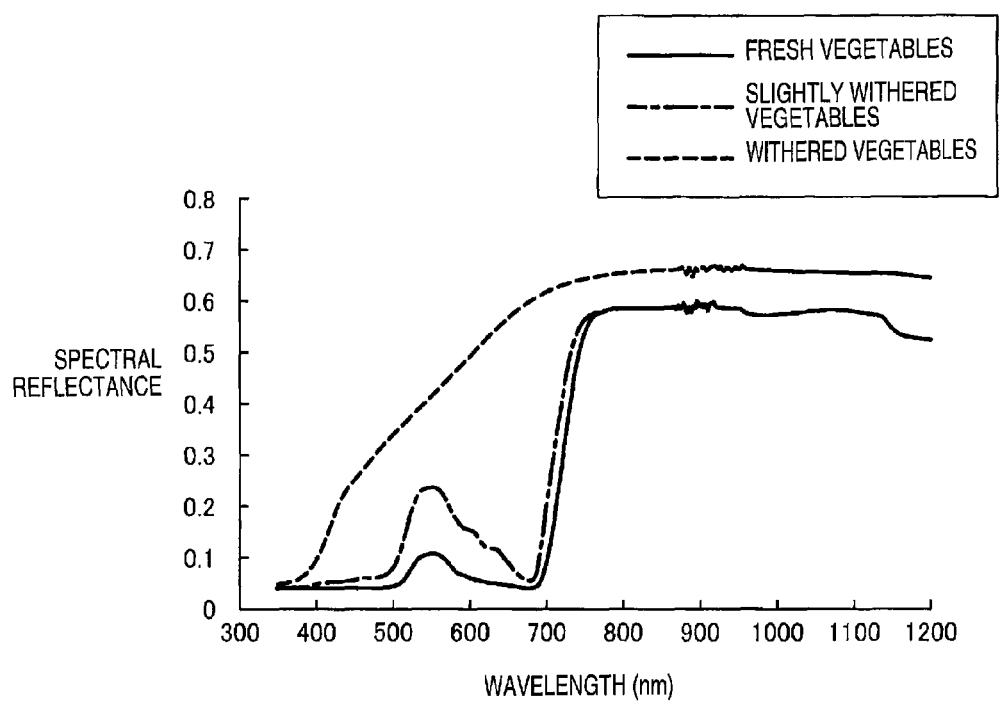
FIG. 2 is a graph showing a relationship between a wavelength and spectral reflectance of light for green vegetables having different freshness from each other.

FIG. 2 is a graph showing a relationship between a wavelength and the spectral reflectance of light for green vegetables having different freshness from each other. As shown in the drawing, a spectrum waveform varies between fresh vegetables, slightly withered vegetables, and withered vegetables. With the fresh vegetables and the slightly withered vegetables, reflectance rapidly decreases in a wavelength range of a boundary of approximately 700 nm and less thereof. The reason thereof is because absorption of the light occurs due to chlorophyll having a wavelength of equal to or less than 700 nm. On the other hand, with the withered vegetables, since the amount of chlorophyll is decreased, the reflectance significantly increases particularly in a wavelength range of 700 nm or less. As described above, the spectrum of each sample is measured in the step 2, as the freshness of the green vegetables changes the spectrum waveform.

In addition, instead of measuring the spectral reflectance spectrum and the absorbance spectrum with a spectroscope, the spectra may be estimated from other measured values. For example, the sample may be measured with a multiband camera to estimate the spectral reflectance or absorbance spectrum from the obtained multiband image. As such an estimating method, a method disclosed in JP-A-2001-99710 can be used, for example.

Step 3

A step 3 is a measurement step of the chlorophyll amount and is performed by the operator. The operator performs chemical analysis of each of the plurality of samples prepared in the step 1, to measure the chlorophyll amount which is the content of the target component of each sample. Specifically, a predetermined portion is extracted from each sample and chlorophyll which is the target component is extracted from the predetermined portion to measure the amount thereof. Herein, the "predetermined portion" may be any portion of the sample, but it preferably coincides with the portion used when measuring the spectrum in the step 2.

Step 4

Figure 3A:
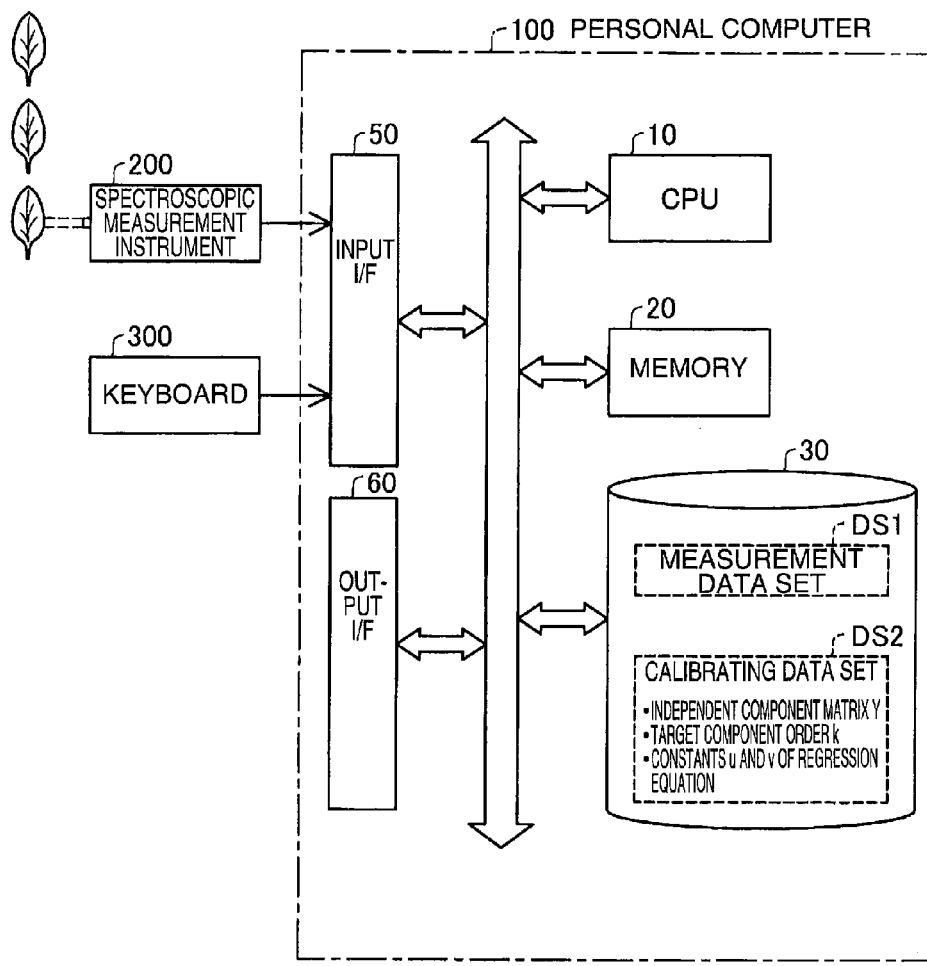
FIG. 3A is an explanatory diagram showing a personal computer and peripheral devices used in a step 4 and a step 5.

A step 4 is an estimation step of a mixing coefficient and is performed using a personal computer. FIG. 3A is an explanatory diagram showing a personal computer 100 and peripheral devices used in the step 4 and a step 5 which will be described later. As shown in the drawing, the personal computer (hereinafter, simply referred to as a "computer") 100 is electrically connected to the spectroscopic measurement instrument 200 and a keyboard 300.

The computer 100 is a well-known device which includes a CPU 10 which performs various processes or control by executing a computer program (hereinafter, simply referred to as a "program"), a memory 20 (storage unit) which is a data saving location, a hard disk drive 30 which stores program, data, or information, an input interface (I/F) 50, and an output interface (I/F) 60.

Figure 3B:
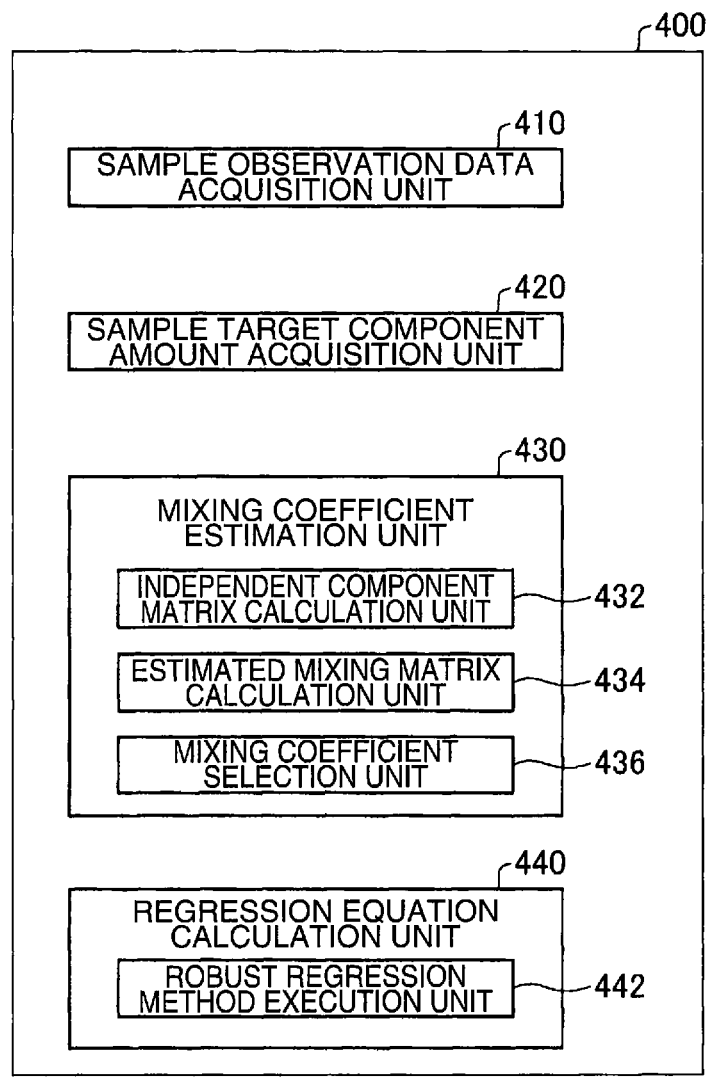
FIG. 3B is a functional block diagram of a device used in a step 4 and a step 5.

FIG. 3B is a functional block diagram of a device used in the step 4 and the step 5. This device 400 includes a sample observation data acquisition unit 410, a sample target component amount acquisition unit 420, a mixing coefficient estimation unit 430, and a regression equation calculation unit 440. The mixing coefficient estimation unit 430 includes an independent component matrix calculation unit 432, an estimated mixing matrix calculation unit 434, and a mixing coefficient selection unit 436. The regression equation calculation unit 440 includes a robust regression method execution unit 442. The sample observation data acquisition unit 410 and the sample target component amount acquisition unit 420 are implemented by the CPU 10 of FIG. 3A in cooperation with the input I/F 50 and the memory 20, for example. The mixing coefficient estimation unit 430, the independent component matrix calculation unit 432, the estimated mixing matrix calculation unit 434, and the mixing coefficient selection unit 436 are implemented by the CPU 10 of FIG. 3A in cooperation with the memory 20, for example. In addition, the regression equation calculation unit 440 and the robust regression method execution unit 442 are implemented by the CPU 10 of FIG. 3A in cooperation with the memory 20, for example. These units can also be implemented by another specific apparatus or a hardware circuit other than the personal computer shown in FIG. 3A.

Figure 3C:
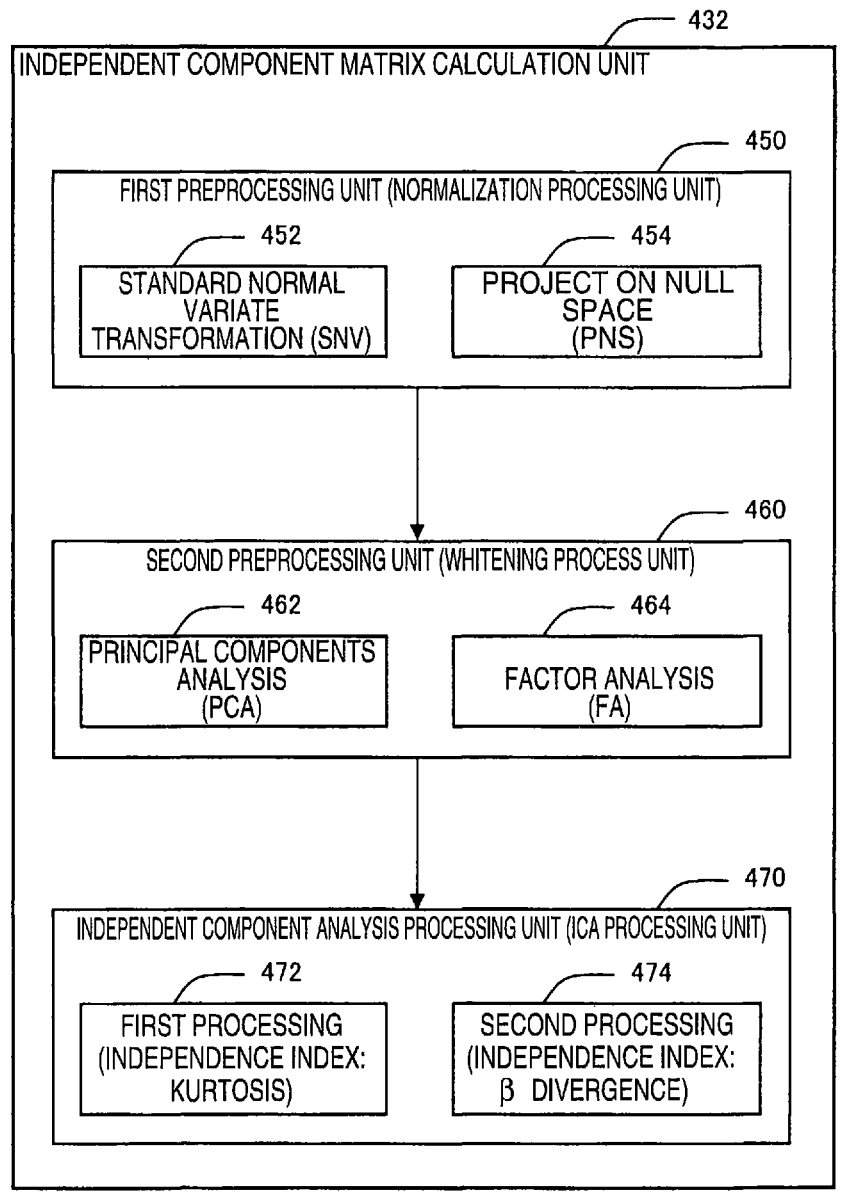
FIG. 3C is a functional block diagram showing an example of an internal configuration of an independent component matrix calculation unit.

FIG. 3C is a functional block diagram showing an example of an internal configuration of the independent component matrix calculation unit 432. The independent component matrix calculation unit 432 includes a first preprocessing unit 450, a second preprocessing unit 460, and an independent component analysis processing unit 470. The three processing units 450, 460, and 470 acquire an independent component matrix (which will be described later) by processing data to be processed (absorbance spectrum in the embodiment) in this order. Processing content of each unit will be described later.

The spectroscopic measurement instrument 200 shown in FIG. 3A is the instrument used in the step 2. The computer 100 acquires the absorbance spectrum obtained from a spectral distribution measured by the spectroscopic measurement instrument 200 in the step 2, through the input I/F 50 as spectral data (corresponding to the sample observation data acquisition unit 410 of FIG. 3B). The computer 100 acquires the chlorophyll amount measured in the step 3 through the input I/F 50 through manipulation of the keyboard 300 by the operator (corresponding to the sample target component amount acquisition unit 420 of FIG. 3B). The chlorophyll amount measured in the step 3 may be input to the computer 100 as a chlorophyll mass in terms of a unit mass (for example, for each 100 grams) of the predetermined portion used when measuring the chlorophyll. Alternatively, the chlorophyll amount may be input as an absolute value of mass.

As a result of acquisition of the spectral data and the chlorophyll amount, a data set (hereinafter, referred to as a "measurement data set") DS1 including the spectral data and the chlorophyll amount is stored in the hard disk drive 30 of the computer 100.

Figure 4:
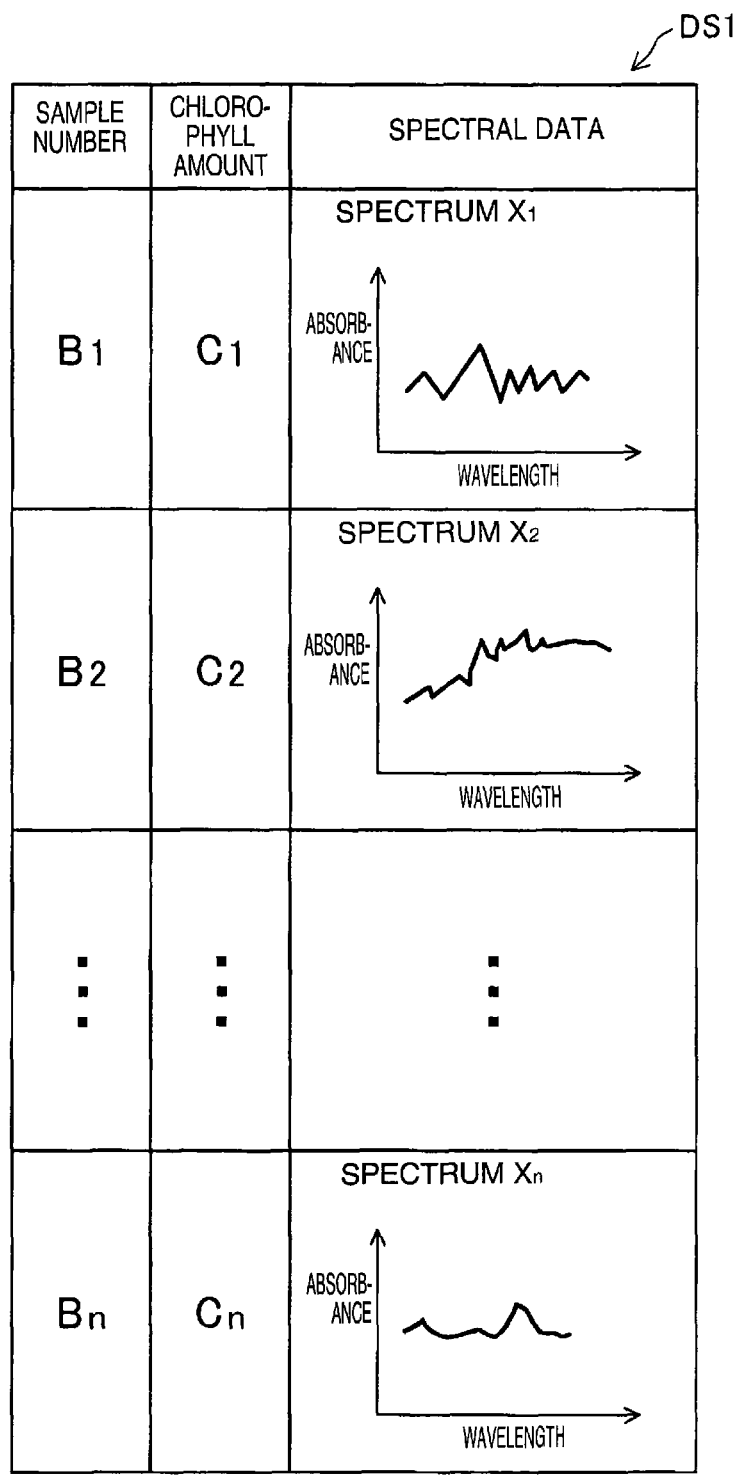
FIG. 4 is an explanatory diagram schematically showing a measurement data set stored in a hard disk drive.

FIG. 4 is an explanatory diagram schematically showing the measurement data set DS1 stored in the hard disk drive 30. As shown in the drawing, the measurement data set DS1 has a data structure including sample numbers $B_1$, $B_2$, ..., $B_n$ for identifying the plurality of samples prepared in the step 1, chlorophyll amounts $C_1$, $C_2$, ..., $C_n$ of each sample, and spectral data items $X_1$, $X_2$, ..., $X_n$ of each sample. In the measurement data set DS1, the samples numbers $B_1$, $B_2$, ..., $B_n$ are given to the chlorophyll amounts $C_1$, $C_2$, ..., $C_n$, and spectral data items $X_1$, $X_2$, ..., $X_n$, so as to determine which sample the amount and the data item are for.

The CPU 10 performs a process of estimating the mixing coefficient which is an operation of the step 4, by loading a predetermined program stored in the hard disk drive 30 into the memory 20 and executing the program. Herein, the predetermined program can be downloaded using a network such as the Internet from the outside. In the step 4, the CPU 10 functions as the mixing coefficient estimation unit 430 of FIG. 3B.

Figure 5:
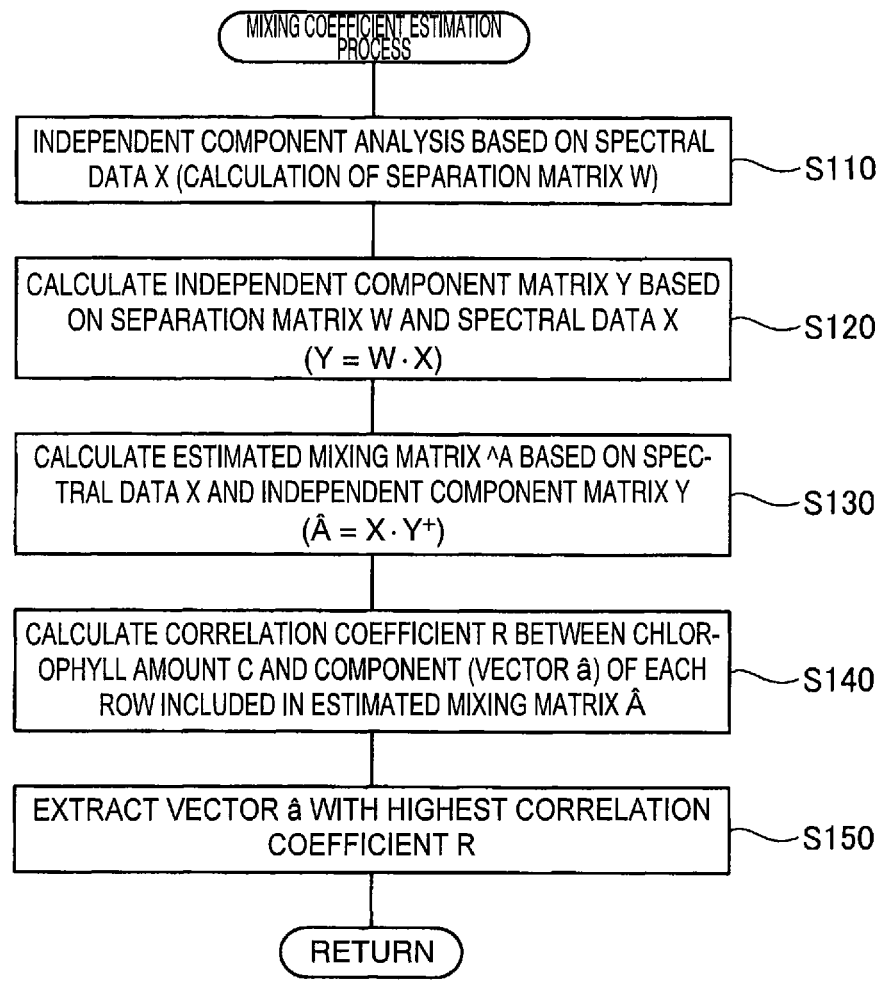
FIG. 5 is a flowchart showing a mixing coefficient estimation process performed by a CPU.

FIG. 5 is a flowchart showing a mixing coefficient estimation process performed by the CPU 10. When the process is started, the CPU 10, first, performs the independent component analysis (Step S110).

Independent component analysis (ICA) is one of multidimensional signal analysis methods, and is a technology of observing a mixed signal on which an independent signal is superimposed, under several different conditions, and separating an independent original signal from the mixed signal based thereon. If independent component analysis is used, by recognizing the spectral data obtained by the step 2 as data in which m independent components (unknown) such as chlorophyll are mixed with each other, the spectra of the independent components can be estimated from the spectral data (observation data) obtained by the step 2.

In the embodiment, the independent component analysis is performed by performing the process of the three processing units 450, 460, and 470 shown in FIG. 3C in this order. The first preprocessing unit 450 can perform preprocessing using one or both of standard normal variate transformation (SNV) 452 and project on null space (PNS) 454. The SNV 452 is a process of subtracting an average value of data to be processed and dividing a resultant value by a standard deviation thereof, to obtain normalized data in which an average value is 0 and the standard deviation is 1. The PNS 454 is a process for removing baseline variation included in the data to be processed. In measurement of the spectrum, variation between data items, called baseline variation, such as an increase or a decrease of the average value of the data for each measurement data item occurs due to various reasons. Accordingly, it is preferable to remove the reasons for the variation before performing the independent component analysis process. The PNS can be used as preprocessing which can remove the arbitrary baseline variation. In addition, the PNS is, for example, illustrated in "Extracting Chemical Information from Spectral Data with Multiplicative Light Scattering Effects by Optical Path-Length Estimation and Correction", Zeng-Ping Chen, Julian Morris, and Elaine Martin, 2006.

It is not necessary to perform the process by the PNS 454 in a case of performing the SNV 452 with respect to the spectral data obtained in the step 2 of FIG. 1. On the other hand, in a case of performing the PNS 454, it is preferable to perform any normalization process (for example, SNV 452) after that.

A process other than the SNV or the PNS may be performed as the first preprocessing. In the first preprocessing, it is preferable to perform any normalization process, but the normalization process may be omitted. Hereinafter, the first preprocessing unit 450 is also called a "normalization processing unit". The content of the two processes 452 and 454 will be further described. The first preprocessing can also be omitted in a case where the data to be processed which is applied to the independent component matrix calculation unit 432 is normalized data.

The second preprocessing unit 460 can perform preprocessing using any one of principal components analysis (PCA) 462 and factor analysis (FA) 464. A process other than the PCA or the FA may be used as the second preprocessing. Hereinafter, the second preprocessing unit 460 is also called a "whitening processing unit". In the typical ICA method, dimensional compression of the data to be processed and non-correlating are performed, as the second preprocessing. Since a transformation matrix to be acquired in the ICA is limited to an orthogonal transformation matrix by the second preprocessing, it is possible to decrease computational complexity of the ICA. Such a second preprocessing is called "whitening" and the PCA is used in many cases. However, in a case where random noise is included in the data to be processed, the PCA may be affected by an effect thereof, and accordingly error may be generated in a result. Herein, in order to decrease the effect of the random noise, it is preferable to perform the whitening using the FA having robustness with respect to the noise, instead of the PCA. The second preprocessing unit 460 of FIG. 3C can perform the whitening by selecting any one of the PCA and the FA. The content of the two processes 462 and 464 will be further described later. In addition, the whitening process may be omitted.

The independent component analysis processing unit (ICA processing unit) 470 performs the ICA with respect to the spectral data which is subjected to the first preprocessing and the second preprocessing, to estimate a spectrum of the independent component. The ICA processing unit 470 can perform analysis using any one of the first processing 472 which uses a kurtosis as an independence index, and the second processing 474 which uses β divergence as an independence index. As an index for separating the independent components, the ICA generally uses higher order statistics representing independence between the separated data items as the independence index. The kurtosis is a typical independence index. However, in a case where an outlier such as spike noise is included in the data to be processed, statistics including the outlier are calculated as the independence index. Therefore, an error may be generated between original statistics and the calculated statistics of the data to be processed, and this may cause a decrease in separation accuracy. Herein, in order to decrease an effect from the outlier in the data to be processed, it is preferable to use the independence index which is hardly affected by the effect thereof. β divergence can be used as the independence index having such properties. The content of the kurtosis and the β divergence will be further described later. An index other than the kurtosis or the β divergence may be used as the independence index of the ICA.

Next, typical processing content of the independent component analysis will be described in detail. Spectra S of m unknown components (sources) (hereinafter, this spectra may be simply referred to as "unknown components") are assumed to be applied by a vector of the following formula (2), and n spectral data items X obtained by the step 2 are assumed to be applied by a vector of the following formula (3). In addition, each of elements ($S_1, S_2, \ldots, S_m$) included in the formula (2) is set to be the vector (spectrum). That is, the element $S_1$ is represented as a formula (4), for example. Elements ($X_1, X_2, \ldots, X_n$) included in the formula (3) are also the vectors, and the element $X_1$ is represented as a formula (5), for example. An index 1 is the number of wavelength bands in which the spectra are measured. The number of elements m of the spectra S of the unknown components is an integer equal to or larger than 1, and is empirically and experimentally determined in advance based on the type of the sample (herein, spinach).

$$s=[s_1, s_2, \ldots, s_m]^T \tag{2}$$

$$x=[x_1, x_2, \ldots, x_n]^T \tag{3}$$

$$S=\{S_{11}, S_{12}, \ldots, S_{1l}\} \tag{4}$$

$$X=\{X_{11}, X_{12}, \ldots, X_{1l}\} \tag{5}$$

Each unknown component is assumed to be independent statistically. A relationship of the following formula (6) is satisfied between the unknown components S and the spectral data items X.

$$X=A \cdot S \tag{6}$$

A of the formula (6) is the mixing matrix, and can also be represented by the following formula (7). Herein, it is necessary to show a latter "A" as a thick letter as shown in the formula (7), but it is shown as a normal letter herein due to limitation of letters of the specification. Hereinafter, other thick letters representing the matrix are shown as the normal letters, in the same manner.

$$A = \begin{pmatrix} a_{11} & \cdots & a_{1m} \\ \vdots & \ddots & \vdots \\ a_{n1} & \cdots & a_{nm} \end{pmatrix} \tag{7}$$

A mixing coefficient $a_{ij}$ included in the mixing matrix A represents a contribution degree of an unknown component $S_j$ (j=1 to m) to spectral data $X_i$ (i=1 to n) which is the observation data.

In a case where the mixing matrix A is known, a least squares solution of the unknown component S can be simply acquired as $A^+ \cdot X$ using a pseudo inverse matrix $A^+$ of A, but in a case of the first embodiment, since the mixing matrix A is also unknown, it is necessary to estimate the unknown component S and the mixing matrix A only from the observation data X. That is, as shown in the following formula (8), a matrix (hereinafter, referred to as an "independent component matrix") Y showing the spectrum of the independent component is calculated using a separation matrix W of m×n, only from the observation data X. As an algorithm for acquiring this separation matrix W of the following formula (8), various algorithms such as Infomax, Fast Independent Component Analysis (FastICA), Joint Approximate Diagonalization of Eigenmatrices (JADE), and the like can be used.

$$Y=W \cdot X \tag{8}$$

The independent component matrix Y corresponds to an estimated value of the unknown component S. Accordingly, the following formula (9) can be obtained, and the following formula (10) can be obtained by transforming the formula (9).

$$X=\hat{A} \cdot Y \tag{9}$$

$$\hat{A}=X \cdot Y^+ \tag{10}$$

Herein, ^A is an estimated mixing matrix of A and $Y^+$ is a pseudo inverse matrix of Y.

The estimated mixing matrix ^A (denoted as this due to limitation of letters of the specification, but actually meaning the letter with attached symbol on a left side of the formula (10), this applies to the other letters) obtained with the formula (10) can be represented by the following formula (11).

$$\hat{A} = \begin{pmatrix} \hat{a}_{11} & \cdots & \hat{a}_{1m} \\ \vdots & \ddots & \vdots \\ \hat{a}_{n1} & \cdots & \hat{a}_{nm} \end{pmatrix} \tag{11}$$

In Step S110 of FIG. 5, the CPU 10 performs the process up to a process of acquiring the separation matrix W described above. In detail, the spectral data X of each sample which is obtained in the step 2 and is previously stored in the hard disk drive 30 is input, and the separation matrix W is acquired based on this input, using any algorithm such as Infomax, FastICA, or JADE described above. As shown in FIG. 3C described above, it is preferable to perform the normalization process by the first preprocessing unit 450 and the whitening process by the second preprocessing unit 460, as the preprocessing of the independent component analysis.

After performing Step S110, the CPU 10 performs a process of calculating the independent component matrix Y, based on the separation matrix W and the spectral data X of each sample which is obtained in the step 2 and is previously stored in the hard disk drive 30 (Step S120). This calculation process is a process of performing an arithmetic operation according to the formula (8). In the processes of Steps S110 and S120, the CPU 10 functions as the independent component matrix calculation unit 432 of FIG. 3B.

Next, the CPU 10 performs a process of calculating the estimated mixing matrix ^A, based on the spectral data X of each sample which is previously stored in the hard disk drive 30, and the independent component matrix Y which is calculated in Step S120 (Step S130). This calculation process is a process of performing an arithmetic operation according to the formula (10).

FIG. 6 is an explanatory diagram for illustrating the estimated mixing matrix ^A. A table TB shown in the drawing includes the sample numbers $B_1, B_2, \ldots, B_n$ in a vertical direction, and elements (hereinafter, referred to as "independent component elements") $Y_1, Y_2, \ldots, Y_m$ of the independent component matrix Y in a horizontal direction. An element in the table TB which is specified from the sample number $B_i$ (i=1 to n) and the independent component element $Y_j$ (j=1 to m), is the same as a coefficient $^\wedge\alpha_{ij}$ included in the estimated mixing matrix ^A (see the formula (11)). From the table TB, it is found that the coefficient $^\wedge\alpha_{ij}$ included in the estimated mixing matrix ^A represents each ratio of the independent component elements $Y_1, Y_2, \ldots, Y_m$ of each sample. A target component order k shown in FIG. 6 will be described later. In the process of Step S130, the CPU 10 functions as the estimated mixing matrix calculation unit 434 of FIG. 3B.

The estimated mixing matrix ^A is obtained by the process up to Step S130. That is, the coefficients (estimated mixing coefficient) $^\wedge\alpha_{ij}$ included in the estimated mixing matrix ^A are obtained. After that, the process proceeds to Step S140.

In Step S140, the CPU 10 acquires a correlation (degree of similarity) between the chlorophyll amounts $C_1, C_2, \ldots, C_n$ measured in the step 3, and a component (hereinafter, referred to as a vector $^\wedge\alpha$) of each row included in the estimated mixing matrix ^A calculated in Step S130. In detail, a correlation between the chlorophyll amount C $(C_1, C_2, \ldots, C_n)$ and the vector $^\wedge\alpha_1$ $(^\wedge\alpha_{11}, ^\wedge\alpha_{21}, \ldots, ^\wedge\alpha_{n1})$ of a first row is acquired, then, a correlation between the chlorophyll amount C $(C_1, C_2, \ldots, C_n)$ and the vector $^\wedge\alpha_2$ $(^\wedge\alpha_{12}, ^\wedge\alpha_{22}, \ldots, ^\wedge\alpha_{n2})$ of a second row is acquired, and by doing so, a correlation of each row with respect to the chlorophyll amount C is subsequently acquired, and lastly, a correlation between the chlorophyll amount C $(C_1, C_2, \ldots, C_n)$ and the vector $^\wedge\alpha_m$ $(^\wedge\alpha_{1m}, ^\wedge\alpha_{2m}, \ldots, ^\wedge\alpha_{nm})$ of an m-th row is acquired.

The correlations can be acquired by a correlation coefficient R according to the following formula (12). The correlation coefficient R is called Pearson's product-moment correlation coefficient.

$$R = \frac{\sum_{i=1}^{n}(C_i - \overline{C})(\hat{a}_{ik} - \overline{\hat{a}}_k)}{\sqrt{\sum_{i=1}^{n}(C_i - \overline{C})^2}\sqrt{\sum_{i=1}^{n}(\hat{a}_{ik} - \overline{\hat{a}}_k)^2}} \quad (12)$$

$\overline{C}$ and $\overline{^\wedge\alpha}_k$ each represent a chlorophyll amount and an average value of a vector $^\wedge\alpha_k$.

Figure 7A:
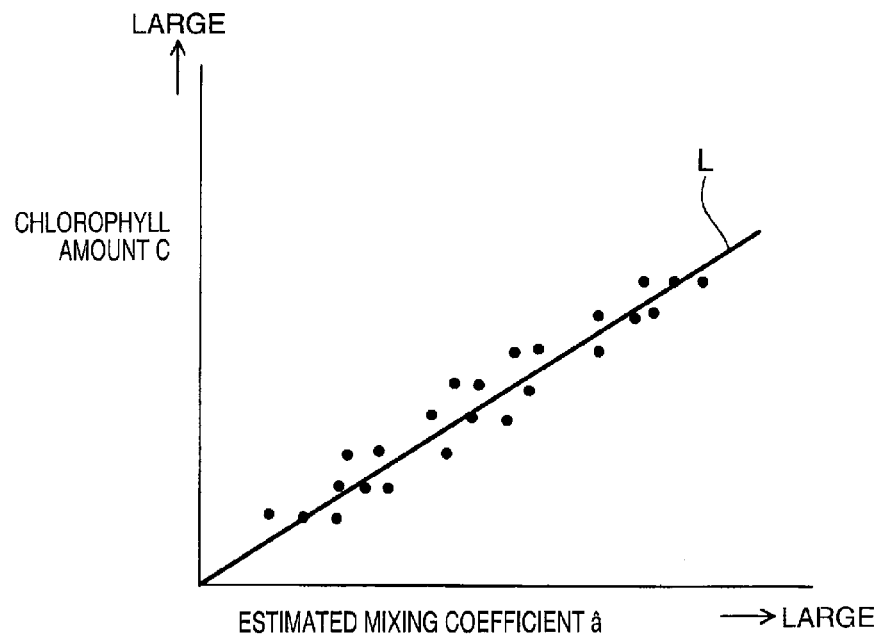
FIG. 7A is an explanatory diagram showing an example of a scatter diagram having a high correlation.
Figure 7B:
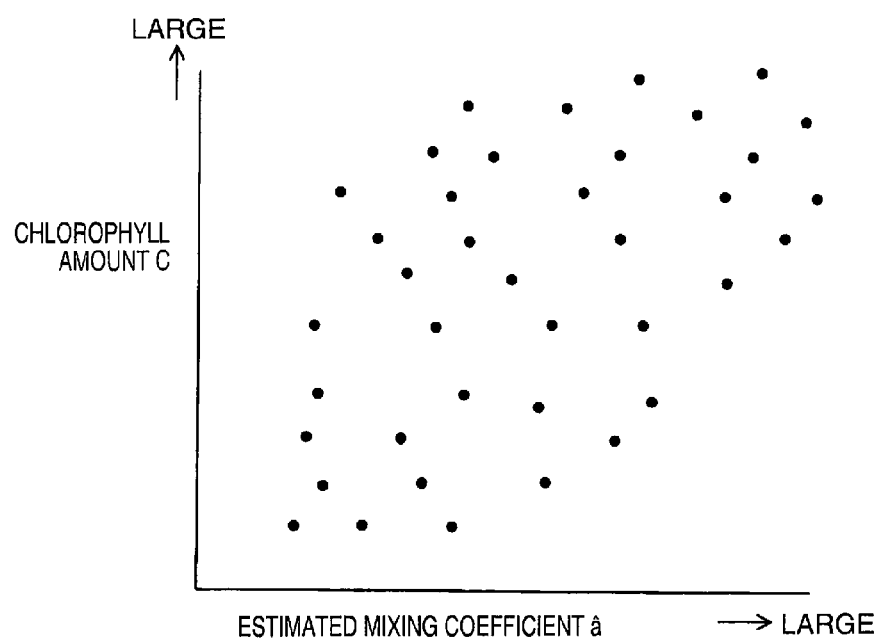
FIG. 7B is an explanatory diagram showing an example of a scatter diagram having a low correlation.

FIG. 7A is a graph of a scatter diagram. The scatter diagram of the drawing includes the chlorophyll amount C on a vertical axis, and a coefficient of the estimated mixing matrix ^A (hereinafter, referred to as an "estimated mixing coefficient") ^a on a horizontal axis. Points specified from each element $C_1, C_2, \ldots, C_n$ of the chlorophyll amount C and the estimated mixing coefficients $^\wedge\alpha_{1j}, ^\wedge\alpha_{2j}, \ldots, ^\wedge\alpha_{nj}$ (j=1 to m) included in the vector $^\wedge\alpha$ in the vertical direction of the estimated mixing matrix ^A are plotted. In the example shown in the drawing, plotted points are relatively concentrated in a vicinity of a linear line L. In this case, the correlation between the chlorophyll amount C and the estimated mixing coefficient ^a is high. In contrast, when the correlation between the chlorophyll amount C and the estimated mixing coefficient ^a is decreased, the plotted points are not aligned linearly, but are widely scattered, as shown in FIG. 7B. That is, as the correlation between the chlorophyll amount C and the estimated mixing coefficient ^a increases, the plotted points have an increasing tendency to be concentrated linearly. The correlation coefficient R shown in the formula (12) represents a degree of the tendency of the plotted points to be concentrated linearly.

As a result of Step S140 of FIG. 5, a correlation coefficient $R_j$ (j=1, 2, ..., m) of each independent component (independent component spectrum) $Y_j$ is obtained. After that, the CPU 10 specifies a correlation coefficient having highest correlation, that is, having a value close to 1, from the correlation coefficients $R_j$ obtained in Step S140. In a case of the scatter diagram described above, the correlation coefficient $R_j$ which is obtained with plotted points most concentrated in a linear shape, is specified. The row vector $^\wedge\alpha$ with which the highest correlation coefficient R is obtained, is selected from the estimated mixing matrix ^A (Step S150).

In the case of the Table TB of FIG. 6, the selection in Step S150 is selection of one row from the plurality of rows. An element of the selected row is a mixing coefficient of the independent component corresponding to chlorophyll which is the target component. As a result of the selection, the vector $^\wedge\alpha_k$ $(^\wedge\alpha_{1k}, ^\wedge\alpha_{2k}, \ldots, ^\wedge\alpha_{nk})$ is obtained. Herein, k is any integer of 1 to m. A value of k is temporarily stored in the memory 20 as the target component order which shows what number of the independent component corresponds to the target component. Each of $^\wedge a_{1k}, ^\wedge a_{2k}, \ldots, ^\wedge a_{nk}$ included in the vector $^\wedge\alpha_k$ correspond to the "mixing coefficients corresponding to the target component" in Application Example 1. In the example of FIG. 6, target component order k=2 shows the row vector $^\wedge\alpha_2 = (^\wedge a_{12}, ^\wedge a_{22}, \ldots, ^\wedge a_{n2})$ corresponding to the independent component $Y_2$. In the present specification, a term "order" is used with a meaning of a "value showing a position in the matrix". In the processes of Steps S140 and S150, the CPU 10 functions as the mixing coefficient selection unit 436 of FIG. 3B. After performing Step S150, the CPU 10 ends the calculation process of the mixing coefficients. As a result, the step 4 ends and then the process proceeds to the step 5.

Step 5

The step 5 is a calculation step of a regression equation, and is performed using the computer 100 in the same manner as during the time of performing the step 4. In the step 5, the computer 100 performs a process of calculating the regression equation of the calibration curve. The step 5 may be performed by transferring the data which is subjected to the process up to the step 4, to another computer.

Figure 8:
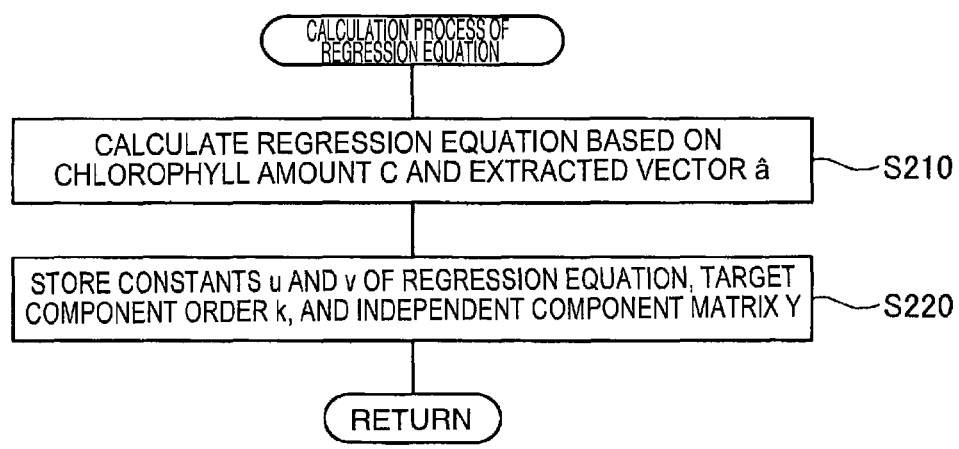
FIG. 8 is a flowchart showing a calculation process of a regression equation performed by a CPU of a computer.

FIG. 8 is a flowchart showing the calculation process of the regression equation performed by the CPU 10 of the computer 100. When the process is started, the CPU 10 first calculates a regression equation F, based on the chlorophyll amount C ($C_1, C_2, \ldots, C_n$) measured in the step 3, and the vector $\hat{\alpha}_k$ ($\hat{a}_{1k}, \hat{a}_{2k}, \ldots, a_{nk}$) selected in Step S150 (Step S210). In a case where the scatter diagram shown in FIG. 7A has high correlation, the linear line L in the drawing corresponds to the regression equation F. The calculation method of the regression equation F performed using a least-squares method is well known. That is, the linear line L is acquired using a least-squares method so as to set a distance from the linear line L in the drawing to each plotted point (residual error) to be close to 0, for example. With respect to this, instead of the least-squares method, the embodiment is configured to calculate the regression equation using a robust regression method. The regression equation F can be represented by the following formula (13). In Step S210, constants u and v of the formula (13) are acquired.

$$F: C = u\hat{\alpha}_k + v \quad (13)$$

Figure 9:
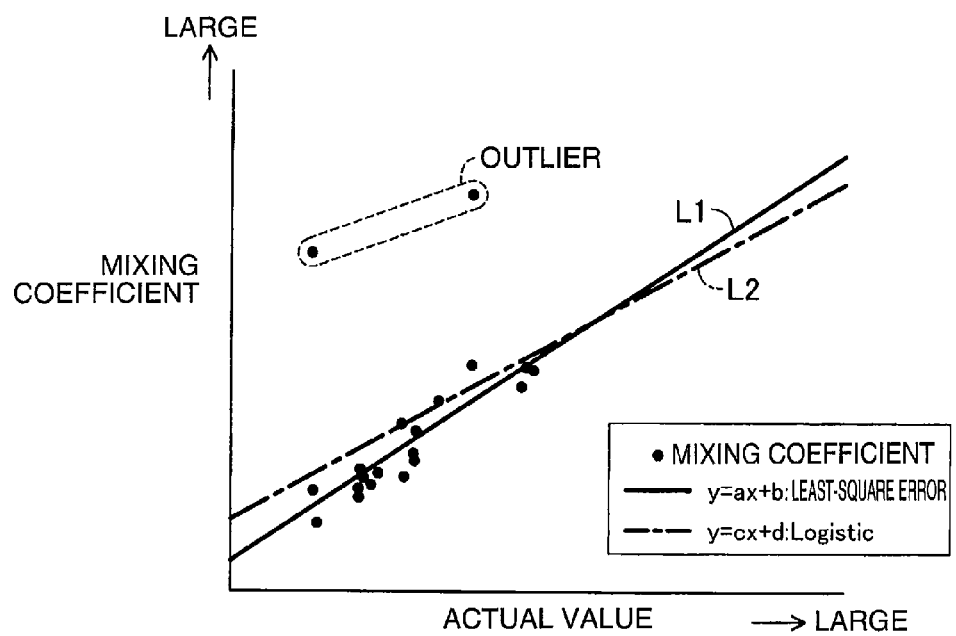
FIG. 9 is a graph for illustrating a robust regression method.

FIG. 9 is a graph for illustrating the robust regression method. The graph shows an actual value x of the chlorophyll amount on a horizontal axis and the mixing coefficient y on a vertical axis. In the drawing, a calibration curve L1 acquired by using the robust regression method is shown with a solid line and a calibration curve L2 acquired by using the least-squares method is shown with a dashed-dotted line. In the least-squares method, the effect of the outlier is significantly shown by only including a few outliers, and the calibration curve L2 which is an approximately linear line is greatly shifted from the distribution center of the plotted points excluding the outliers. In contrast, the robust regression method is configured not to be affected by the outlier as much as possible, and by performing regression by weighting so as to reduce the error with respect to the outlier, it is possible to create the calibration curve L1 which passes through a portion close to the distribution center of the plotted points.

In detail, the robust regression method is a repeated weighted least-squares method in which an approximate line is acquired by the least-squares method, then weighting is performed so as to have a small effect in a case of a long distance of the plotted points from the approximate line and a large effect in a case of a short distance therefrom, and an approximate line is acquired again by the least-squares method. More specifically, as the robust regression method, a method described in a document "Robust Statistics—Theory and Methods—", R. Maronna, R. D. Martin and V. J. Yohai (2006) John Wiley & Sons, Ltd. can be used.

In the embodiment, in detail, the regression equation is calculated by using Robustfit of "Statistics Toolbox" which is an application package of Matlab (trademark), and a logistic function as a weight function.

After calculating the regression equation in Step S210 of FIG. 8, the CPU 10 stores the constants u and v of the regression equation F acquired in Step S210, the target component order k (FIG. 6) obtained in Step S150, and the independent component matrix Y calculated in Step S120 of the calculation process (FIG. 5) of the mixing coefficient, in the hard disk drive 30 as a calibrating data set DS2 (Step S220). After that, the CPU 10 temporarily ends the calculation process of the regression equation by proceeding to a "return" step. As a result, the regression equation of the calibration curve can be acquired, and the calibration curve creating method shown in FIG. 1 also ends. In the processes of Steps S210 and S220, the CPU 10 functions as the regression equation calculation unit 440 and the robust regression method execution unit 442 of FIG. 3B.

B. CALIBRATING METHOD OF TARGET COMPONENT

Next, a calibrating method of the target component will be described. A test object is configured with the same components as the sample used when creating the calibration curve. In detail, the calibrating method of the target component is performed using the computer. In addition, the computer herein may be the computer 100 used when creating the calibration curve or may be another computer.

Figure 10:
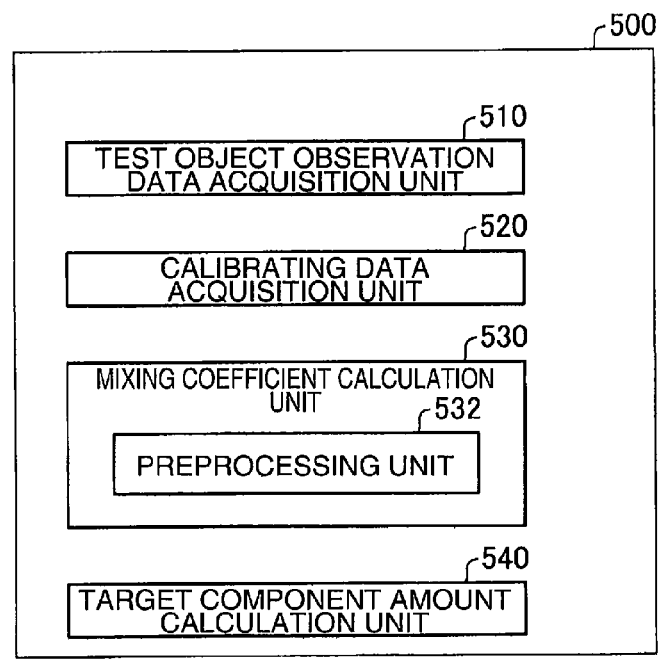
FIG. 10 is a functional block diagram of a device used when performing calibration of a target component.

FIG. 10 is a functional block diagram of a device used when performing the calibration of the target component. This device 500 includes a test object observation data acquisition unit 510, a calibrating data acquisition unit 520, a mixing coefficient calculation unit 530, and a target component amount calculation unit 540. The mixing coefficient calculation unit 530 includes a preprocessing unit 532. The preprocessing unit 532 has functions of both the first preprocessing unit 450 and the second preprocessing unit 460 of FIG. 3C. The test object observation data acquisition unit 510 is implemented by the CPU 10 of FIG. 3A in cooperation with the input I/F 50 and the memory 20, for example. The calibrating data acquisition unit 520 is implemented by the CPU 10 of FIG. 3A in cooperation with the memory 20 and the hard disk drive 30, for example. The mixing coefficient calculation unit 530 and the target component amount calculation unit 540 are implemented by the CPU 10 of FIG. 3A in cooperation with the memory 20, for example. The computer which implements each function of FIG. 10 is set as the computer 100 used when creating the calibration curve, and the calibrating data set DS2 described above is stored in the storage unit such as the hard disk drive or the like.

Figure 11:
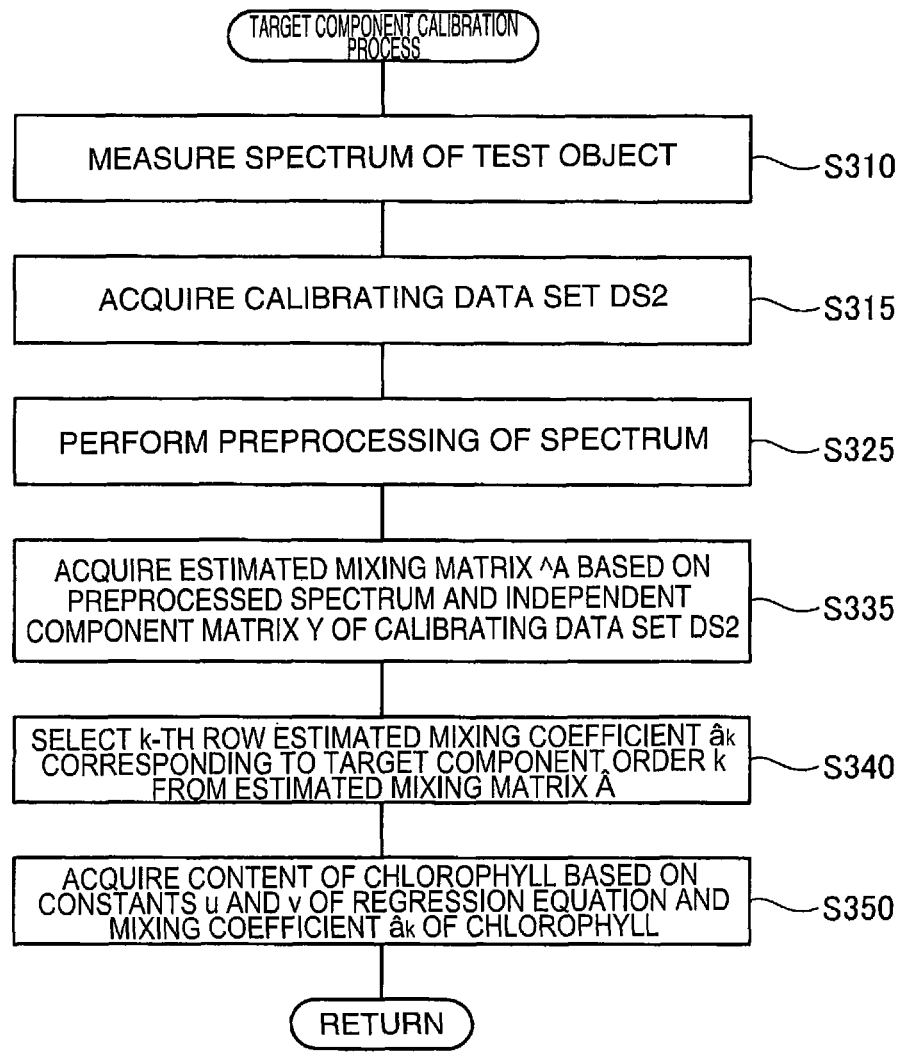
FIG. 11 is a flowchart showing a target component calibration process performed by a CPU of a computer.
Figure 12A:
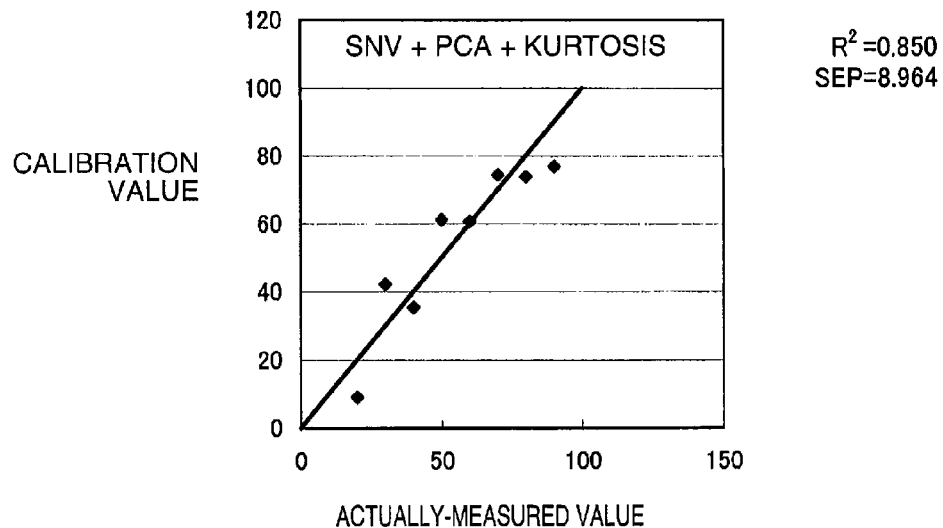
FIG. 12A is a diagram showing calibration accuracy of independent component analysis (algorithm is SNV+PCA+kurtosis) relating to absorbance of a mixture of sucrose and salt.
Figure 12B:
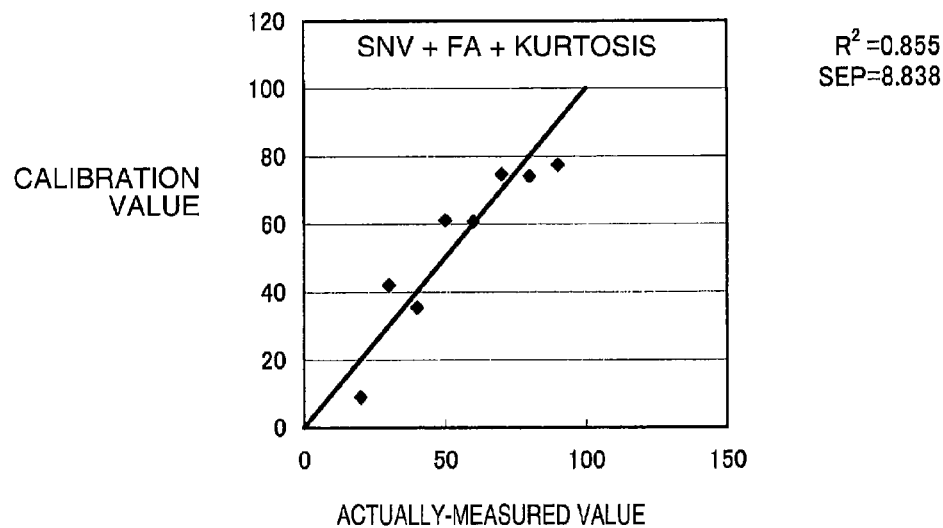
FIG. 12B is a diagram showing calibration accuracy of independent component analysis (algorithm is SNV+FA+kurtosis) relating to absorbance of a mixture of sucrose and salt.
Figure 12C:
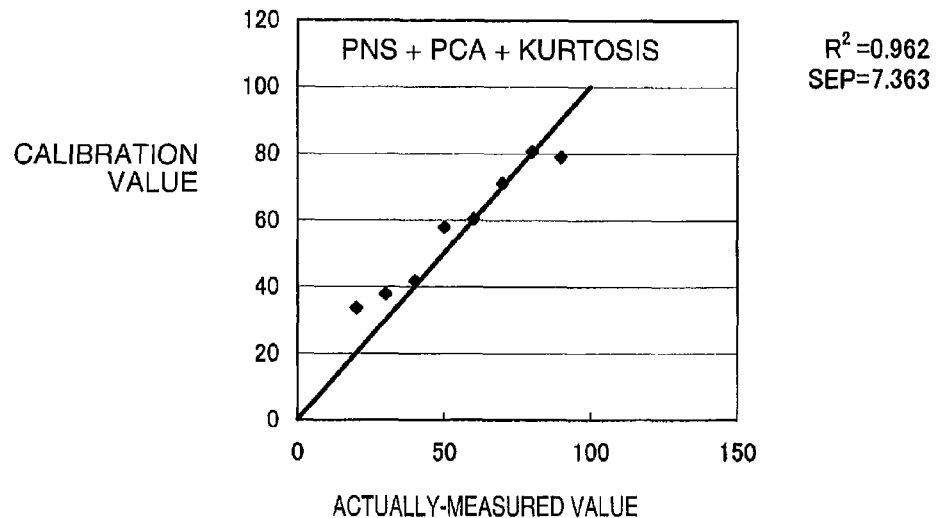
FIG. 12C is a diagram showing calibration accuracy of independent component analysis (algorithm is PNS+PCA+kurtosis) relating to absorbance of a mixture of sucrose and salt.
Figure 12D:
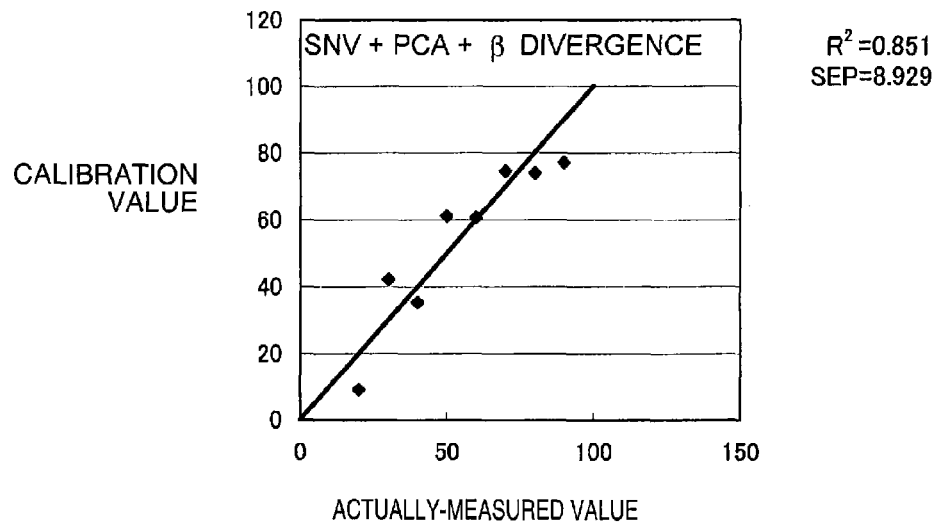
FIG. 12D is a diagram showing calibration accuracy of independent component analysis (algorithm is SNV+PCA+β divergence) relating to absorbance of a mixture of sucrose and salt.
Figure 12E:
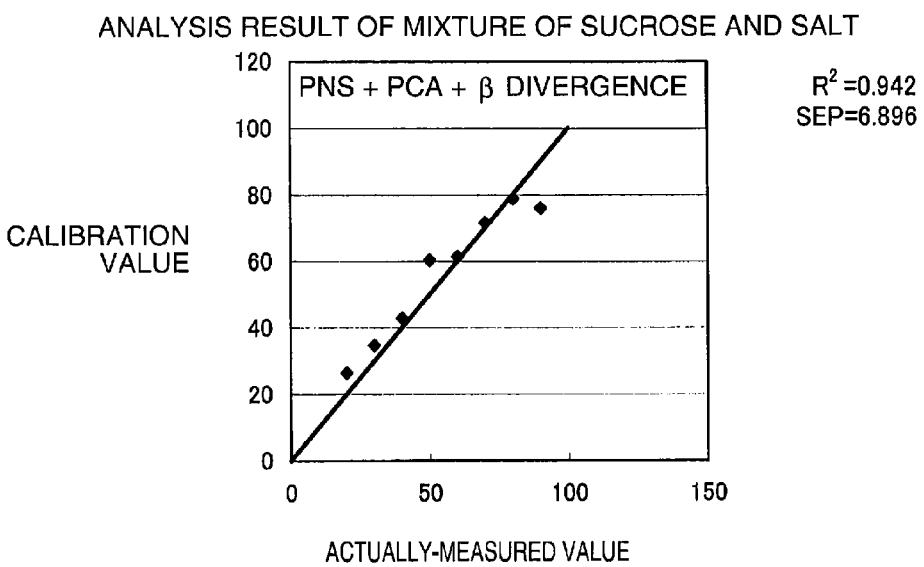
FIG. 12E is a diagram showing calibration accuracy of independent component analysis (algorithm is PNS+PCA+β divergence) relating to absorbance of a mixture of sucrose and salt.
Figure 12F:
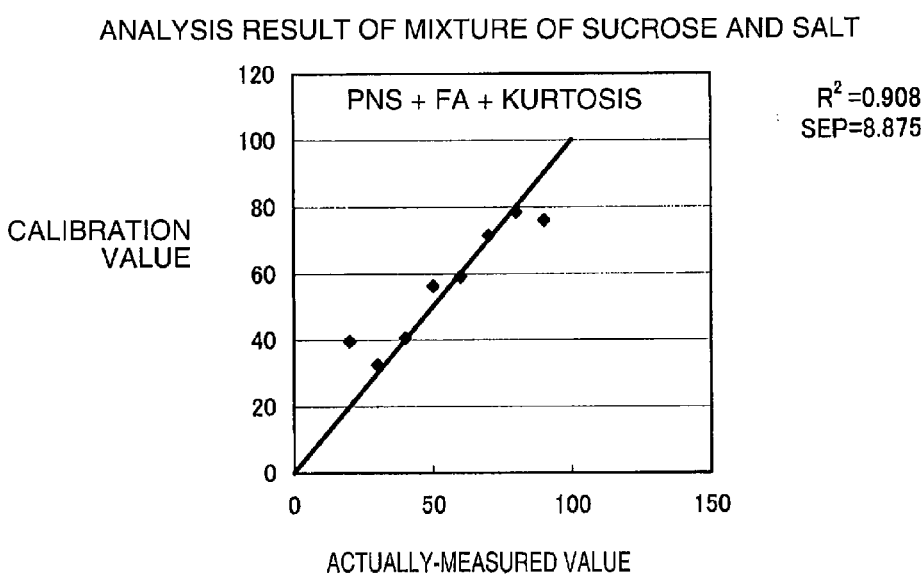
FIG. 12F is a diagram showing calibration accuracy of independent component analysis (algorithm is PNS+FA+kurtosis) relating to absorbance of a mixture of sucrose and salt.
Figure 12G:
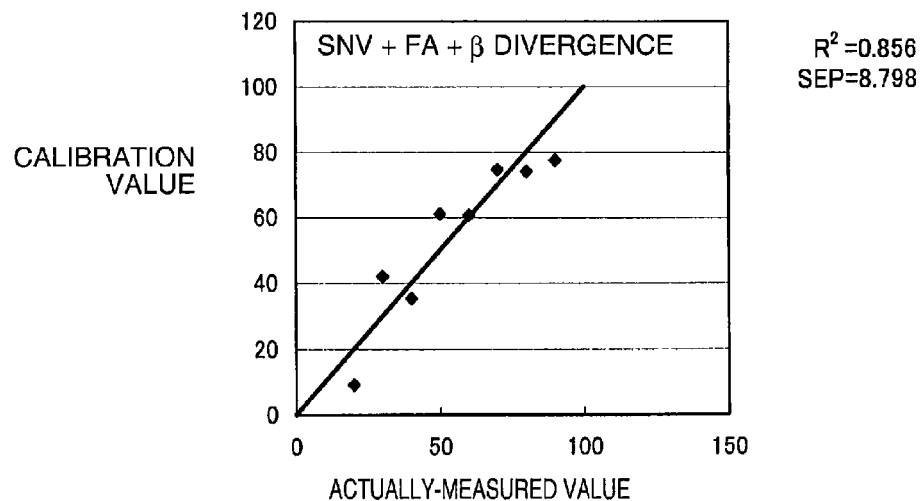
FIG. 12G is a diagram showing calibration accuracy of independent component analysis (algorithm is SNV+FA+β divergence) relating to absorbance of a mixture of sucrose and salt.
Figure 12H:
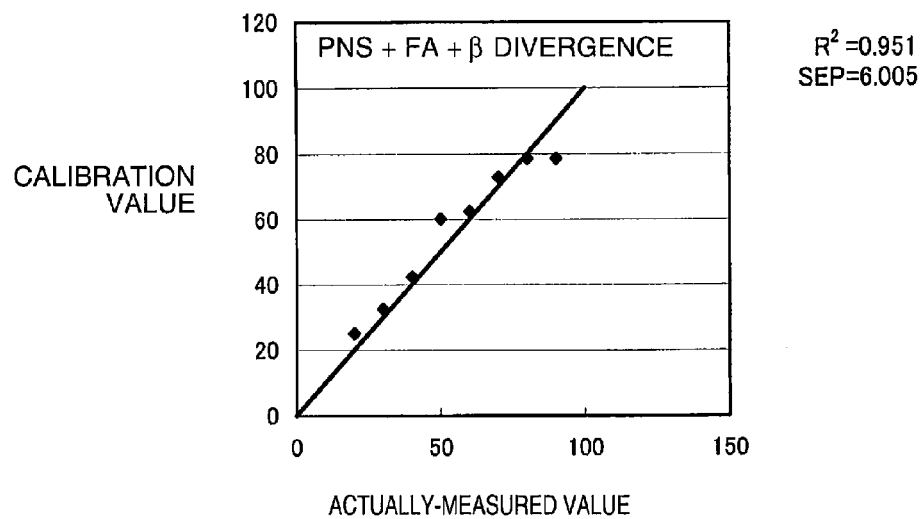
FIG. 12H is a diagram showing calibration accuracy of independent component analysis (algorithm is PNS+FA+β divergence) relating to absorbance of a mixture of sucrose and salt.
Figure 14A:
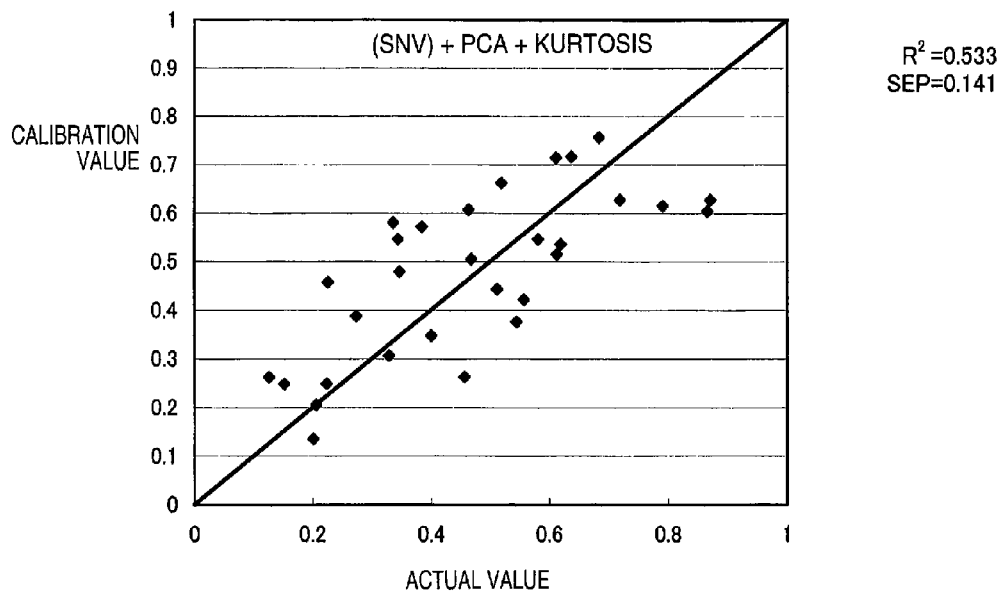
FIG. 14A is a diagram showing calibration accuracy of independent component analysis (algorithm is SNV+PCA+kurtosis) relating to a mixed signal of voices of people.
Figure 14B:
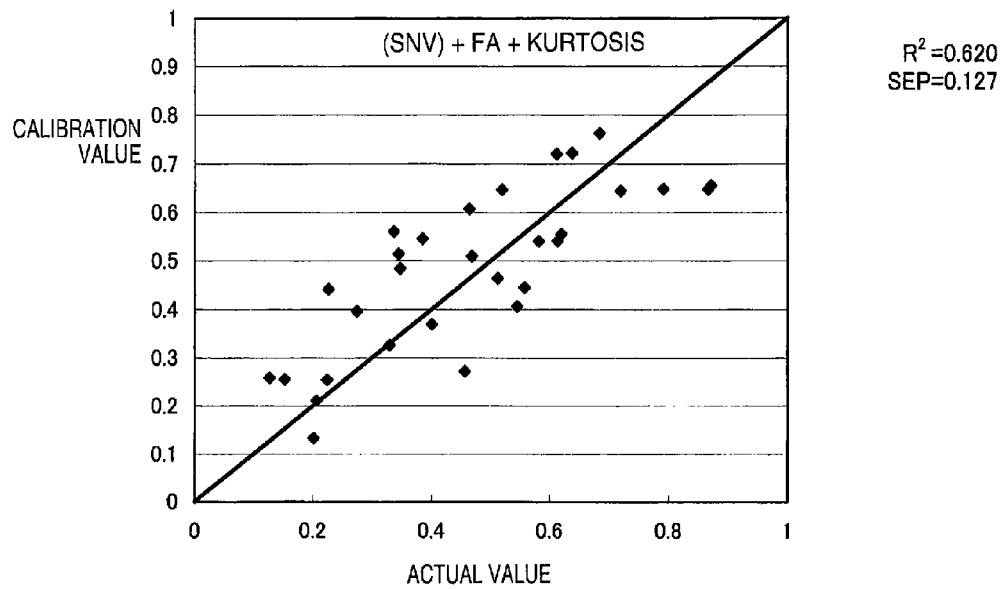
FIG. 14B is a diagram showing calibration accuracy of independent component analysis (algorithm is SNV+FA+kurtosis) relating to a mixed signal of voices of people.
Figure 14C:
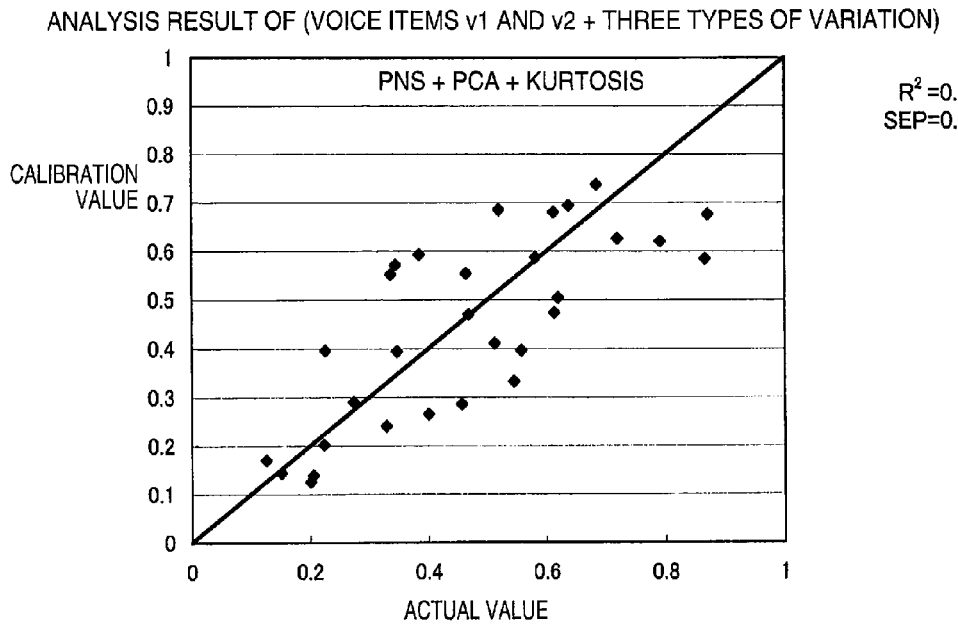
FIG. 14C is a diagram showing calibration accuracy of independent component analysis (algorithm is PNS+PCA+kurtosis) relating to a mixed signal of voices of people.
Figure 14D:
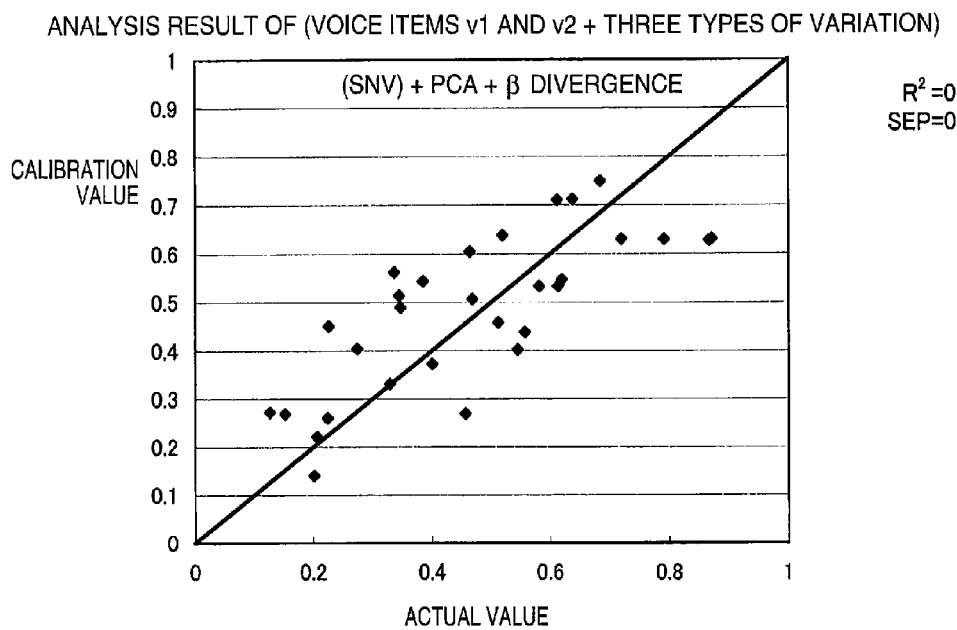
FIG. 14D is a diagram showing calibration accuracy of independent component analysis (algorithm is SNV+PCA+β divergence) relating to a mixed signal of voices of people.
Figure 14E:
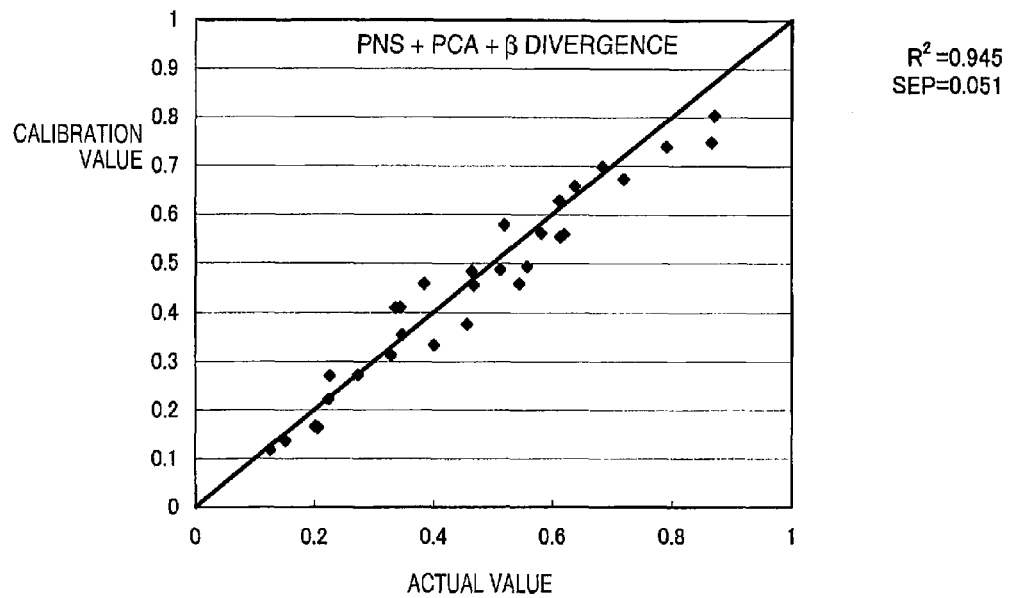
FIG. 14E is a diagram showing calibration accuracy of independent component analysis (algorithm is PNS+PCA+β divergence) relating to a mixed signal of voices of people.
Figure 14F:
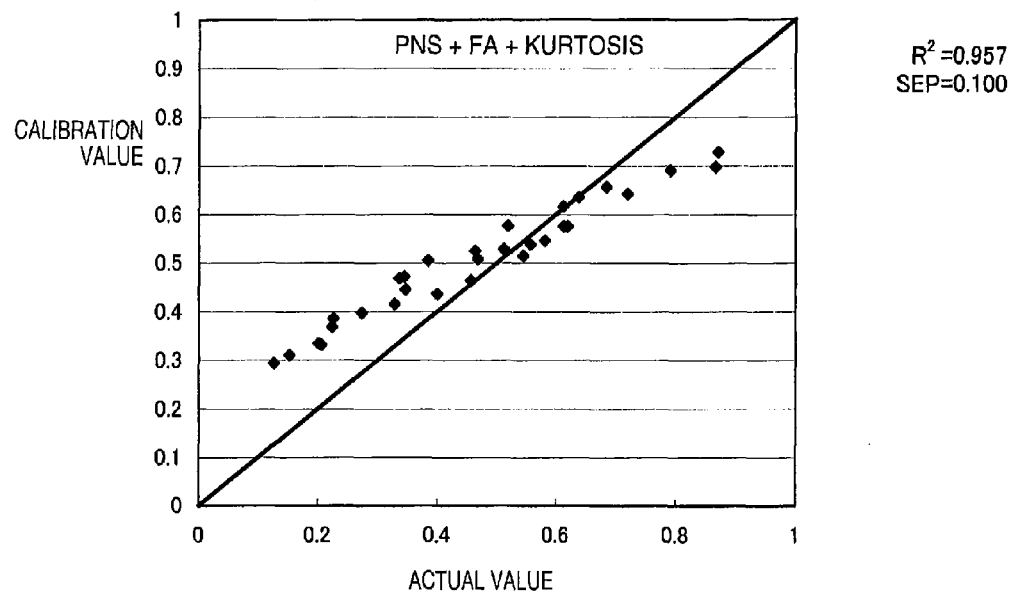
FIG. 14F is a diagram showing calibration accuracy of independent component analysis (algorithm is PNS+FA+kurtosis) relating to a mixed signal of voices of people.
Figure 14G:
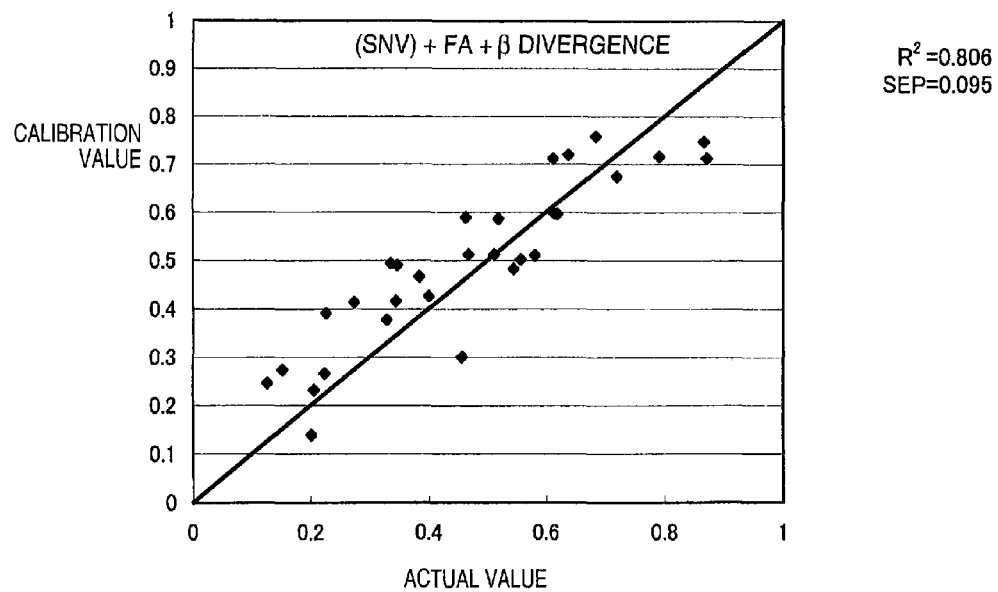
FIG. 14G is a diagram showing calibration accuracy of independent component analysis (algorithm is SNV+FA+β divergence) relating to a mixed signal of voices of people.
Figure 14H:
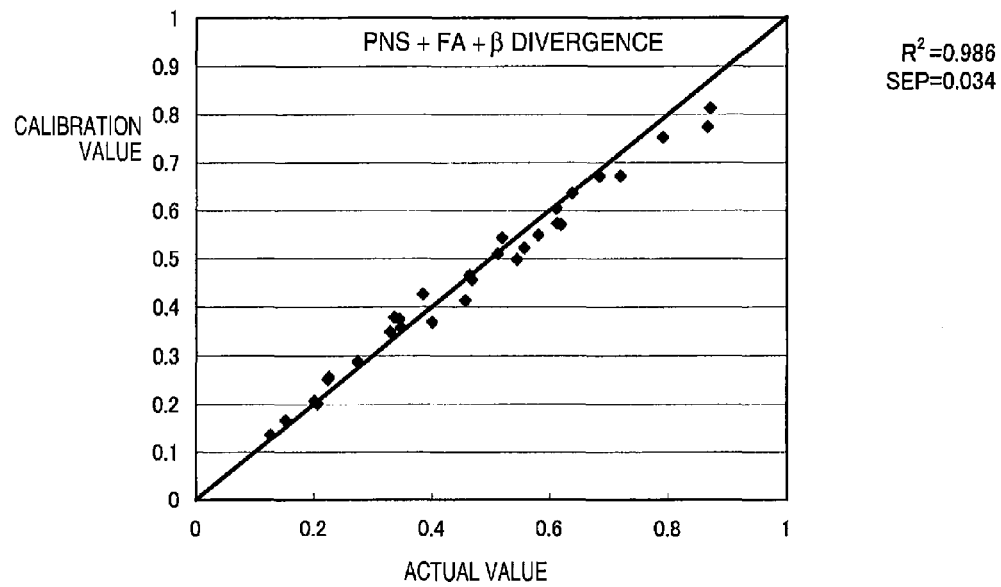
FIG. 14H is a diagram showing calibration accuracy of independent component analysis (algorithm is PNS+FA+β divergence) relating to a mixed signal of voices of people.
Figure 16A:
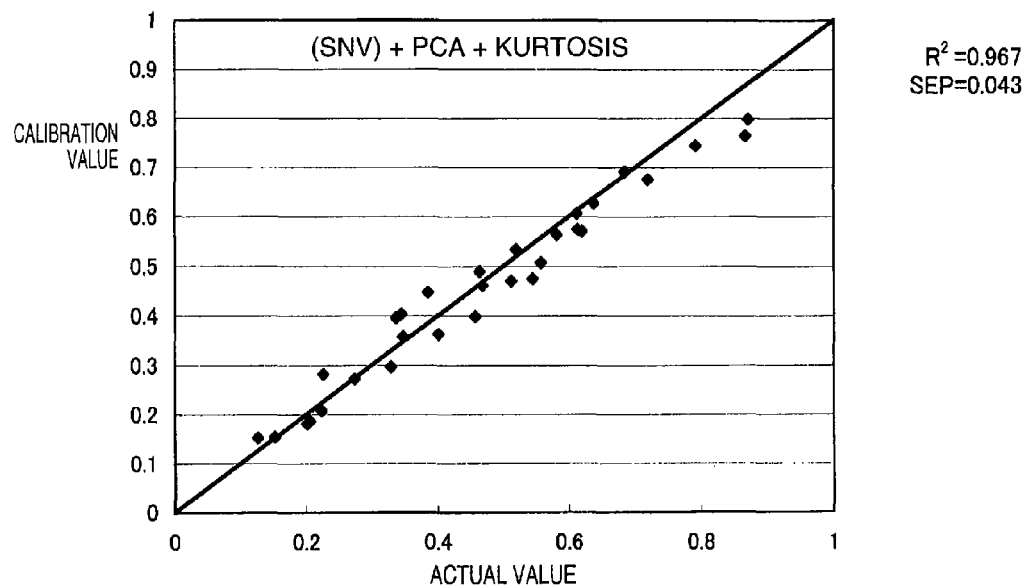
FIG. 16A is a diagram showing calibration accuracy of independent component analysis (algorithm is SNV+PCA+kurtosis) relating to a signal obtained by adding Gaussian noise to a mixed signal of voices of people.
Figure 16B:
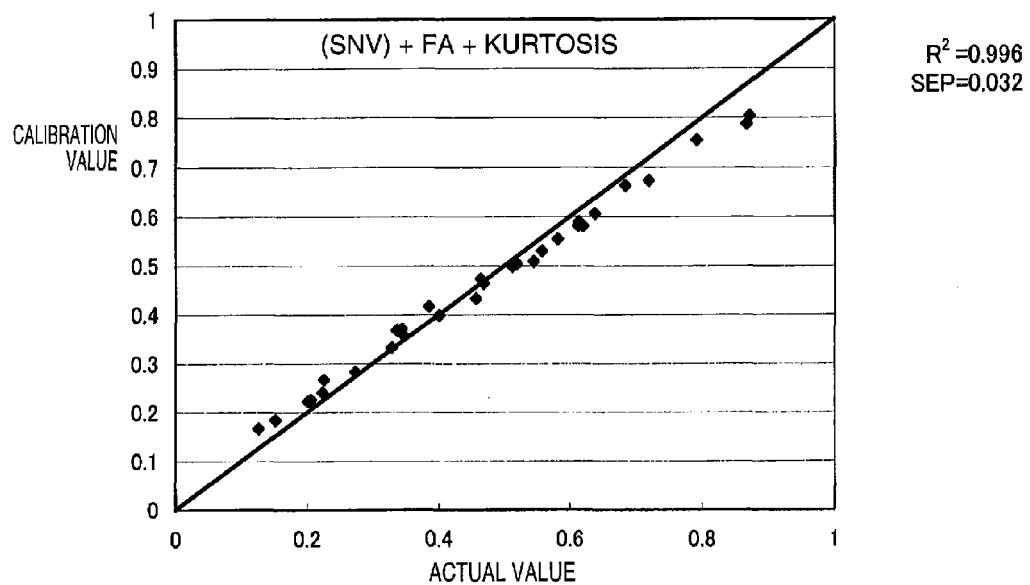
FIG. 16B is a diagram showing calibration accuracy of independent component analysis (algorithm is SNV+FA+kurtosis) relating to a signal obtained by adding Gaussian noise to a mixed signal of voices of people.
Figure 16C:
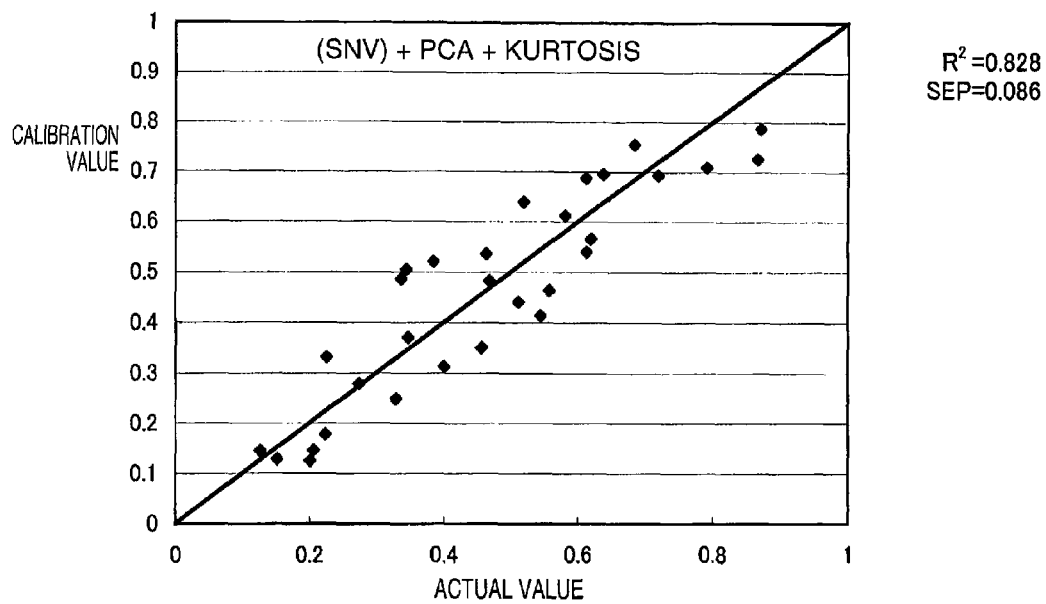
FIG. 16C is a diagram showing calibration accuracy of independent component analysis (algorithm is SNV+PCA+kurtosis) relating to a signal obtained by adding baseline variation to a mixed signal of voices of people.
Figure 16D:
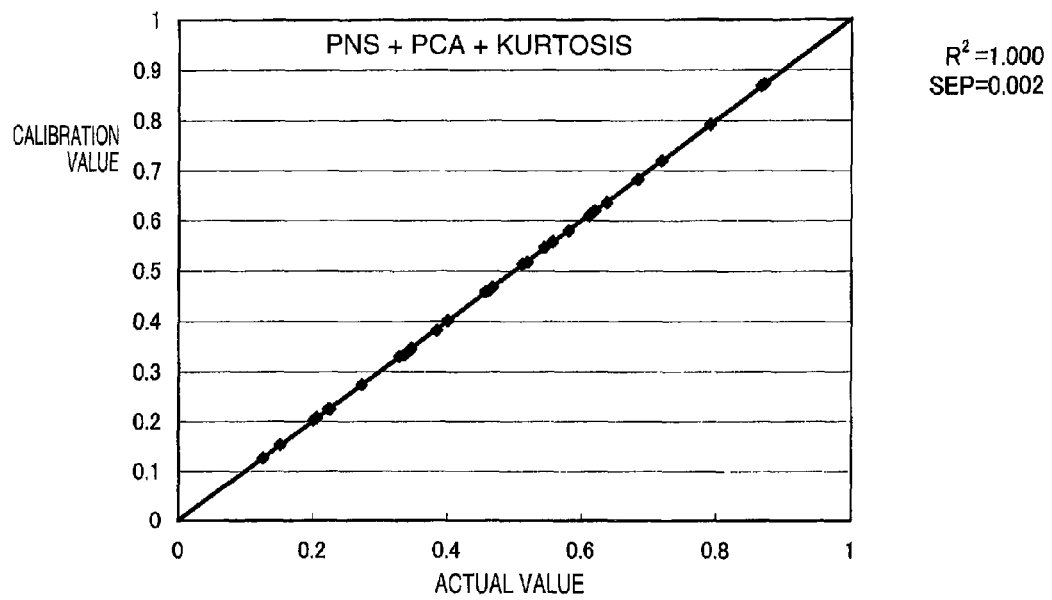
FIG. 16D is a diagram showing calibration accuracy of independent component analysis (algorithm is PNS+PCA+kurtosis) relating to a signal obtained by adding baseline variation to a mixed signal of voices of people.
Figure 16E:
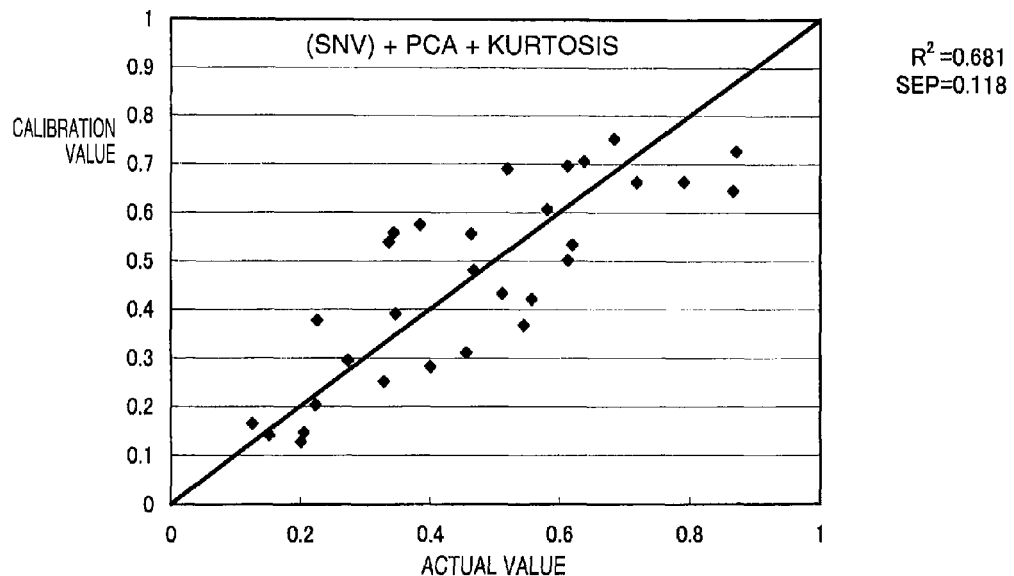
FIG. 16E is a diagram showing calibration accuracy of independent component analysis (algorithm is SNV+PCA+kurtosis) relating to a signal obtained by adding spike noise to a mixed signal of voices of people.
Figure 16F:
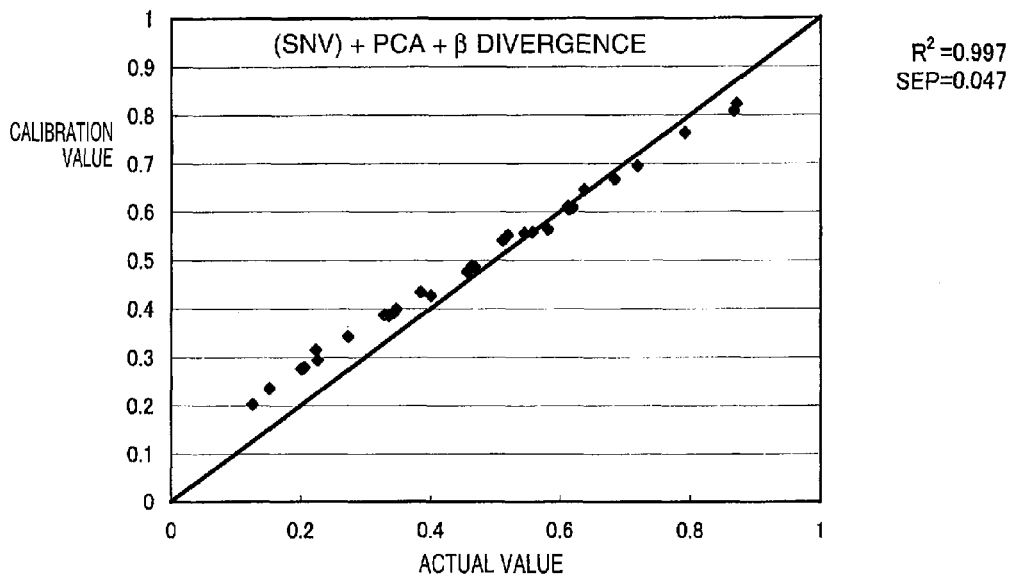
FIG. 16F is a diagram showing calibration accuracy of independent component analysis (algorithm is SNV+PCA+β divergence) relating to a signal obtained by adding spike noise to a mixed signal of voices of people.

FIG. 11 is a flowchart showing a target component calibration process performed by the CPU 10 of the computer 100. The target component calibration process is implemented by loading a predetermined program stored in the hard disk drive 30 into the memory 20 and executing the program by the CPU 10. As shown in the drawing, if the process is started, first, the CPU 10 performs a process of imaging the green vegetables which are the test object with the spectroscopic measurement instrument (Step S310). The imaging in Step S310 can be performed in the same manner as in the step 2, and as a result, an absorbance spectrum $X_p$ of the test object is obtained. For the spectroscopic measurement instrument used in the calibration process, it is preferable to use the same type as that of the spectroscopic measurement instrument used in creating the calibration curve, in order to suppress error. In order to further suppress error, it is more preferable to use the same instrument. In the same manner as in the step 2 of FIG. 1, instead of measuring the spectral reflectance spectrum or the absorbance spectrum with a spectroscope, the spectrum may be estimated from other measured values. The absorbance spectrum $X_p$ of the test object which is obtained when one test object is imaged once, is represented by a vector as in the following formula (14).

$$X_p = \{X_{p1}, X_{p2}, \ldots, X_{pl}\} \quad (14)$$

In the process of Step S310, the CPU 10 functions as the test object observation data acquisition unit 510 of FIG. 10. Next, the CPU 10 acquires the calibrating data set DS2 from the hard disk drive 30 and stores the calibrating data set in the memory 20 (Step S315). In the process of Step S315, the CPU 10 functions as the calibrating data acquisition unit 520 of FIG. 10.

After performing Step S315, the preprocessing is performed with respect to the absorbance spectrum $X_p$ of the test object which is obtained in Step S310 (Step S325). As this preprocessing, it is preferable to perform the same process as the preprocessing (that is, normalization process by the first preprocessing unit 450 and the whitening process by the second preprocessing unit 460) used in the step 4 of FIG. 1 (more specifically, Step S110 of FIG. 5) when creating the calibration curve.

After that, the CPU 10 performs the process of acquiring the estimated mixing matrix ˆA of the test object, based on the independent component matrix Y included in the calibrating data set DS2 and the preprocessed spectrum obtained in Step S325 (Step S335). In detail, since the arithmetic process according to the formula (10) is performed, an inverse matrix (pseudo inverse matrix) $Y^+$ of the independent component matrix Y included in the calibrating data set DS2 is acquired, and the pseudo inverse matrix $Y^+$ is applied to the preprocessed spectrum obtained in Step S325, to acquire the estimated mixing matrix ˆA.

As shown in the following formula (15), the estimated mixing matrix ˆA in the calibration process is a row vector (1×m matrix) which is formed of the mixing coefficients corresponding to each independent component. Herein, after performing Step S335, the CPU 10 reads out the target component order k included in the calibrating data set DS2 from the hard disk drive 30, extracts the mixing coefficient ˆ$α_k$ of a k-th component corresponding to the target component order k, from the estimated mixing matrix ˆA acquired in Step S335, and temporarily stores the mixing coefficient ˆ$α_k$ in the memory 20 as a mixing coefficient of chlorophyll which is the target component (Step S340). In the processes of Steps S325, S335, and S340, the CPU 10 functions as the mixing coefficient calculation unit 530 of FIG. 10.

$$\hat{A} = (\hat{α}_1, \hat{α}_2, \ldots, \hat{α}_m) \quad (15)$$

Next, the CPU 10 reads out the constants u and v of the regression equation included in the calibrating data set DS2 from the hard disk drive 30 and substitutes the constants u and v and the mixing coefficient ˆ$α_k$ of chlorophyll which is the target component obtained in Step S340 into the right side of the formula (13), to acquire the content C of the chlorophyll (Step S350). The content C is acquired as the mass of chlorophyll with respect to a unit mass (for example, for each 100 grams) of the test object. In the process of Step S350, the CPU 10 functions as the target component amount calculation unit 540 of FIG. 10. After that, the target component calibration process ends by proceeding to a "return" step.

In the first embodiment, the content C (mass per unit mass) acquired in Step S350 is set as the content of chlorophyll of the test object, but instead of this, the content C acquired in Step S350 may be corrected with the normalized coefficient used in the normalization in Step S325 and the corrected value may be set as the content to be acquired. In detail, an absolute value (grams) of the content may be acquired by multiplying the standard deviation by the content C. According to this configuration, the content C can have yet further higher accuracy depending on the kinds of the target components.

According to the calibration curve creating method of the first embodiment configured as described above, it is possible to acquire the chlorophyll amount from one spectrum which is an actually-measured value of the green vegetables which are the test object, with high accuracy.

C. VARIOUS ALGORITHMS AND EFFECT THEREOF ON CALIBRATION ACCURACY

Various algorithms used in the first preprocessing unit 450, the second preprocessing unit 460, and the independent component analysis processing unit 470 shown in FIG. 3C, and the effects thereof on the calibration accuracy will be described in order.

C-1. First Preprocessing (Normalization Process Using SNV/PNS)

As the first preprocessing performed by the first preprocessing unit 450, the standard normal variate transformation (SNV) and the project on null space (PNS) can be used.

SNV is given by the following formula (16).

$$z = \frac{x - x_{ave}}{\sigma} \quad (16)$$

Herein, z represents processed data, x represents the data to be processed (absorbance spectrum in the first embodiment) and $x_{ave}$ represents an average value of the data to be processed x, and σ represents a standard deviation of the data to be processed x. As a result of the standard normal variate transformation, the normalized data z in which the average value is 0 and the standard deviation is 1, is obtained.

If the PNS is performed, it is possible to decrease the baseline variation included in the data to be processed. In measurement of the data to be processed (absorbance spectrum in the first embodiment), variation between data items, called baseline variation, such as an increase or a decrease of the average value of the data for each measurement data item occurs due to various reasons. Accordingly, it is preferable to remove the reasons for the variation before performing the independent component analysis process (ICA). The PNS can be used as the preprocessing which can decrease the baseline variation of the data to be processed. In particular, great baseline variation occurs in the measurement data of absorbed light spectrum or reflected light spectrum including the infrared region, and accordingly it is very advantageous to apply the PNS. Hereinafter, a principle of removing the baseline variation included in the data obtained by the measurement (also simply referred to as "measurement data x") by the PNS will be described. In addition, as a typical example, a case where the measurement data is the absorbed light spectrum or the reflected light spectrum including the infrared region, will be described. Herein, the PNS can also be applied, in the same manner, to the other type of the measurement data (for example, voice data or the like).

In general, in an ideal system, the measurement data x (data to be processed x) is represented by the following formula (17), using m (m is an integer equal to or larger than 2) independent components $s_i$ (i=1 to m) and each mixing ratio $c_i$.

$$x = \sum_{i=1}^{m} c_i s_i \quad (17)$$
$$= A \cdot s$$

Herein, A is a matrix (mixing matrix) formed by the mixing ratio $c_i$.

The process is performed also in the independent component analysis (ICA) with this model as a premise. However, various variation factors (change of a state of a specimen or a measurement environment, and the like) exist in the actual measurement data. Herein, as a model obtained by considering those, a model which represents the measurement data x is considered by the following formula (18).

$$x = b\sum_{i=1}^{m} c_i s_i + aE + d\lambda + e\lambda^2 + \varepsilon \tag{18}$$

Herein, b represents a parameter showing a variation amount of the spectrum in an amplitude direction, a, d, and e each represent constant baseline variation E (also referred to as an "average value variation"), a parameter showing an amount of variation $\lambda$ linearly dependent on a wavelength, and a parameter showing an amount of variation $\lambda^2$ secondarily dependent on a wavelength, and $\varepsilon$ represents other variation components. In addition, the constant baseline variation E is given by E={1, 1, 1, ... 1}$^T$, and a data length thereof is a constant vector which is equivalent to a data length (number of sections of the wavelength band) of the measurement data x. The variation $\lambda$ and $\lambda^2$ dependent on the wavelength are given by $\lambda\{\lambda_1, \lambda_2, \ldots \lambda_N\}^T$ and $\lambda^2=\{\lambda_1^2, \lambda_2^2, \ldots, \lambda_N^2\}^T$, and N herein is the data length of the measurement data x. High-order variation which is equal to or higher than tertiary variation can also be considered as the variation dependent on the wavelength, and up to g-order variation kg (g is an integer equal to or larger than 2) can be generally considered. Since the variation components are error factors in the ICA or the calibration, it is desirable to remove the variations in advance.

In PNS, by imaging the measurement data x in a space (null space) not including the variation components by considering a space configured with each of the baseline variation components E, $\lambda$, $\lambda^2$, ... $\lambda^g$ kg described above, it is possible to obtain the data in which the baseline variation components E, $\lambda$, $\lambda^2$, ... $\lambda^g$ kg (g is an integer equal to or larger than 2) are decreased. As the specific arithmetic operation, the processed data z from the PNS is calculated by the following formula (19).

$$z = (1 - PP^+)x = b\sum_{i=1}^{m} c_i k_i + \varepsilon^* \tag{19}$$
$$P = \{1, \lambda, \lambda^2 \ldots \lambda^g\}$$

Herein, $P^+$ is a pseudo inverse matrix of P. $k_i$ is a component obtained by imaging the configuration component $s_i$ of the formula (18) in the null space not including the variation components. In addition, $\varepsilon^*$ is a component obtained by imaging the variation component $\varepsilon$ of the formula (18) in the null space.

If the normalization (for example, SNV) is performed after processing of PNS, it is possible to eliminate an effect on the variation amount b of the spectrum in an amplitude direction of the formula (18).

If ICA is performed with respect to the data which is subjected to the preprocessing by such PNS, the obtained independent component is an estimated value of the component $k_i$ of the formula (19) and is different from the actual configuration component $s_i$. However, the mixing ratio $c_i$ does not change from the original value of the formula (18), and accordingly the calibration process (FIG. 11) using the mixing ratio $c_i$ is not affected. As described above, when the PNS is performed as the preprocessing of ICA, it is difficult to obtain the actual configuration component $s_i$ by the ICA, and therefore applying the PNS to the preprocessing of the ICA is not considered. On the other hand, in the first embodiment, since the calibration process is not affected although the PNS is performed as the preprocessing of the ICA, if the PNS is performed as the preprocessing, it is possible to perform the calibration with higher accuracy.

In addition, the PNS is specifically disclosed, for example, in "Extracting Chemical Information from Spectral Data with Multiplicative Light Scattering Effects by Optical Path-Length Estimation and Correction", Zeng-Ping Chen, Julian Morris, and Elaine Martin, 2006.

C-2. Second Preprocessing (Whitening Process Using PCA/FA)

The principal components analysis (PCA) and the factor analysis (FA) can be used as the second preprocessing performed by the second preprocessing unit 460.

In the typical ICA method, dimensional compression of the data to be processed and non-correlating are performed, as the preprocessing. Since a transformation matrix to be acquired in the ICA is limited to the orthogonal transformation matrix by this preprocessing, it is possible to decrease the computational complexity of the ICA. Such preprocessing is called "whitening" and the PCA is used in many cases. The whitening using the PCA is described, for example, in Chapter 6 of "Independent Component Analysis", Aapo Hyvarinen, Juha Karhumen, Erkki Oja, 2001, John Wiley & Sons, Inc. ("Independent Component Analysis" February 2005, published by Tokyo Denki University Publishing Department).

However, in the PCA, in a case where random noise is included in the data to be processed, the PCA may be affected by the effect of the random noise, and accordingly error may be generated in the processed result. Herein, in order to decrease the effect of the random noise, it is preferable to perform the whitening using the factor analysis (FA) having robustness with respect to the noise, instead of the PCA. Hereinafter, the principle of the whitening by FA will be described.

As described above, in the typical ICA, a linear mixing model (formula (17)) representing the data to be processed x as a linear sum of the configuration component $s_i$ is assumed, and the mixing ratio $c_i$ and the configuration component $s_i$ are acquired. However, the random noise other than the configuration component $s_i$ is added to the actual data, in many cases. Herein, as the model obtained by considering the random noise, a model representing the measurement data x by the following formula (20) is considered.

$$x = A \cdot s + \rho \tag{20}$$

Herein, $\rho$ represents the random noise.

The whitening considering this noise mixing model is performed, and then it is possible to obtain the estimation of the mixing matrix A and the independent component $s_i$ by performing the ICA.

In the FA of the first embodiment, it is assumed that each of the independent components $s_i$ and the random noise $\rho$ is in accordance with normal distribution N (0, Im) and N (0, $\Sigma$). As generally known, a first parameter x1 of the normal distribution N (x1, x2) represents an expected value and a second parameter x2 thereof represents a standard deviation. At that time, since the data to be processed x is the linear sum of a variable in accordance with the normal distribution, the data to be processed x is also in accordance with the normal distribution. Herein, when a covariance matrix of the data to be processed x is set as V[x], the normal distribution of the data to be processed x can be represented as N (0, V[x]). At that time, a likelihood function of the covariance matrix V[x] of the data to be processed x can be calculated in the following order.

First, if it is assumed that the independent components $s_i$ are orthogonal to each other, the covariance matrix V[x] of the data to be processed x is calculated by the following formula (21).

$$V[x]=E[xx^T]=AA^T+\Sigma \quad (21)$$

Herein, $\Sigma$ represents the covariance matrix of the noise p.

As described above, the covariance matrix V[x] can be represented by the mixing matrix A and the covariance matrix $\Sigma$ of the noise. At that time, a log likelihood function L (A, $\Sigma$) is given by the following formula.

$$L(A, \Sigma) = -\frac{n}{2}\{tr((AA^T + \Sigma)^{-1}C) + \log(\det(AA^T + \Sigma)) + m\log 2\pi\} \quad (22)$$

Herein, n represents the number of data items of the data x, m represents the number of independent components, an operator tr represents a trace of the matrix (sum of diagonal components), and an operator det represents a determinant. In addition, C represents a sample covariance matrix acquired by sample calculation from the data x, and is calculated by the following formula.

$$C = \frac{1}{n}\sum_{i=1}^{n} x_i x_i^T \quad (23)$$

The mixing matrix A and the covariance matrix $\Sigma$ of the noise can be acquired by a maximum-likelihood method using the log likelihood function L (A, $\Sigma$) of the formula (22). As the mixing matrix A, a mixing matrix A which is substantially not affected by the random noise $\rho$ of the formula (20) is obtained. This is a basic principle of the FA. As the algorithm of the FA, there are various algorithms using the algorithm other than the maximum likelihood method. Such various FA can also be used in the first embodiment.

Meanwhile, the estimated value obtained by the FA is merely a value of $AA^T$, in a case where the mixing matrix A adapted for this value is determined, the non-correlating of the data can be performed while decreasing the effect of the random noise, but it is difficult to uniquely determine the plurality of configuration components $s_i$ since a degree of freedom of rotation remains. Meanwhile, the ICA is a process of decreasing the degree of freedom of the rotation of the plurality of configuration components $s_i$ so that the plurality of configuration components $s_i$ are orthogonal to each other. Herein, in the first embodiment, an arbitrary property with respect to the remaining rotation is specified by the ICA, using a value of the mixing matrix A acquired by the FA as the whitened matrix (matrix subjected to the whitening). Accordingly, after performing the whitening process which is robust to the random noise, by performing the ICA, the independent configuration components $s_i$ orthogonal to each other can be determined. In addition, as a result of such a process, it is possible to decrease the effect of the random noise and to improve the calibration accuracy related to the configuration components $s_i$.

C-3. ICA (Kurtosis and $\beta$ Divergence as Independence Index)

In the independent component analysis (ICA), as the index for separating the independent components, the higher order statistics representing independence between the separated data items are generally used as the independence index. The kurtosis is a typical independence index. The ICA using the kurtosis as the independence index is, for example, described in Chapter 8 of "Independent Component Analysis", Aapo Hyvarinen, Juha Karhumen, Erkki Oja, 2001, John Wiley & Sons, Inc. ("Independent Component Analysis" February 2005, published by Tokyo Denki University Publishing Department).

However, in a case where an outlier such as spike noise is included in the data to be processed, statistics including the outlier are calculated as the independence index. Therefore, an error may be generated between original statistics and the calculated statistics of the data to be processed, and this may cause a decrease in separation accuracy. Herein, it is preferable to use the independence index which is hardly affected by the effect from the outlier in the data to be processed. $\beta$ divergence can be used as the independence index having such properties. Hereinafter, a principle of the $\beta$ divergence as the independence index in the ICA will be described.

As described above, in the typical ICA, a linear mixing model (formula (17)) representing the data to be processed x as a linear sum of the configuration components $s_i$ is assumed, and the mixing ratio $c_i$ and the configuration component $s_i$ are acquired. An estimated value y of the configuration component s acquired by the ICA is represented as y=W·y using the separation matrix W. At that time, the separation matrix W is desirably an inverse matrix of the mixing matrix A.

Herein, a log likelihood function L (^W) of an estimated value ^W of the separation matrix W can be represented by the following formula.

$$L(\hat{W}) = \frac{1}{N}\sum_{t=1}^{N} l(x(t), \hat{W}) \quad (24)$$

Herein, an element of a summation sign $\Sigma$ is a log likelihood of each data point x (t). This log likelihood function L (^W) can be used as the independence index of the ICA. A method of the $\beta$ divergence is a method of applying a suitable function to the log likelihood function L (^W) to convert the log likelihood function L (^W) so as to suppress the effect of the outlier such as the spike noise in the data.

In a case of using the $\beta$ divergence as the independence index, first, the log likelihood function L (^W) is converted by the following formula using a function $\Phi_\beta$ which is previously selected.

$$L_\Phi(\hat{W}) = \frac{1}{N}\sum_{t=1}^{N} \Phi_\beta(l(x(t), \hat{W})) \quad (25)$$

This function $L_\Phi$(^W) is considered as a new likelihood function.

As the function $\Phi_\beta$ for decreasing the effect of the outlier such as the spike noise, a function in which the function $\Phi_\beta$ decreases in an exponential manner as the value of the log likelihood function (value in brackets of the function $\Phi_\beta$) decreases, is considered. As such a function $\Phi_\beta$, the following formula can be used, for example.

$$\Phi_\beta(z) = \frac{1}{\beta}\{\exp(\beta z) - 1\} \qquad (26)$$

In this function, as the value of $\beta$ increases, a function value with respect to each data point z (log likelihood in the formula (25)) decreases. The value of $\beta$ can be determined empirically, and can be set as approximately 0.1, for example. The function $\Phi_\beta$ is not limited to that of the formula (26), and it is possible to use another function in which, as the value of $\beta$ increases, the function value with respect to each data point z decreases.

When using the $\beta$ divergence as the independence index, it is possible to suitably suppress the effect of the outlier such as the spike noise. In a case where the likelihood function $L_\Phi(\hat{W})$ such as the formula (25) is considered, a pseudo distance among probability distribution which is minimized corresponding to maximization of the likelihood is $\beta$ divergence. If the ICA using the $\beta$ divergence as the independence index is performed, it is possible to decrease the effect of the outlier such as the spike noise to improve the calibration accuracy of the configuration component $s_i$.

The ICA using the $\beta$ divergence is, for example, described in "Robust Blind Source Separation by $\beta$-Divergence" Minami Mihoko, Shinto Eguchi, 2002.

C-4. Evaluation of Effects of Algorithms on Calibration Accuracy (1)

FIG. 12A to FIG. 12H are diagrams showing comparison of calibration accuracy obtained by processes of combination of algorithms under 8 types of different process conditions, and FIG. 13 is a diagram showing collection of the calibration accuracy of FIG. 12A to FIG. 12H. In the effects evaluation, the absorbance of 8 types of mixtures having different mixing ratios of sucrose and salt is measured with a spectrophotometer to acquire the data to be processed, and the calibration curve (similar to that in FIG. 7A) is created in accordance with the procedures of FIG. 5 and FIG. 8. A calibration target is concentration (ratio with respect to unit volume) of sucrose. A reason for converting the absorbance of the mixture into the data to be processed, is for checking the effect of various algorithms with respect to the data to be processed including various variations. FIG. 12A to FIG. 12H each show a relationship between a calibration value obtained when using the calibration curve obtained as described above, and an actual value.

The following two values are used as index values showing the calibration accuracy. $R^2$ is the square of the correlation coefficient R between the actually-measured value and the calibration value obtained by the independent component analysis, and SEP is expected standard error between the actually-measured values and the calibration values obtained by the independent component analysis.

In general, the calibration accuracy is excellent when $R^2$ is large (close to 1), and the calibration accuracy is excellent when the SEP is small.

In process conditions 1, the standard normal variate transformation (SNV) is used in the first preprocessing, the principal components analysis (PCA) is used in the second preprocessing, and the kurtosis is used as the independence index of the independent component analysis (ICA). In process conditions 2, the process is performed in the same manner as the process conditions 1, except for using the factor analysis (FA) in the second preprocessing. In process conditions 3, the process is performed in the same manner as the process conditions 1, except for using the project on null space (PNS) in the first preprocessing. In a case of using the PNS in the first preprocessing (process conditions 3, 5, 6, and 8), the SNV is performed after the PNS.

Effect of Usage of Project on Null Space (PNS) in First Preprocessing

An effect of usage of the PNS in the first preprocessing can be recognized, when the process conditions 1 and the process conditions 3 of FIG. 13 are compared to each other. That is, with the process conditions 3 in which the PNS is used in the first preprocessing, both the correlation coefficient R and the expected standard error SEP are improved and the calibration accuracy is improved, compared to the process conditions 1 in which only the SNV is used. This effect can also be recognized substantially in the same manner from the comparison between the process conditions 4 and the process conditions 5 or the comparison between the process conditions 7 and the process conditions 8. As described above, the PNS is the algorithm having a great effect for decreasing the effect of the baseline variation. In eight analysis results shown in FIG. 13, the absorbance spectrum including the infrared region is set as a process target as the measurement data. In particular, great baseline variation occurs in the measurement data of absorbance light spectrum or reflected light spectrum including the infrared region, and accordingly it is very advantageous to apply the PNS.

Effect of Usage of Factor Analysis (FA) in Second Preprocessing

An effect of usage of the FA in the second preprocessing can be recognized, when the process conditions 1 and the process conditions 2 of FIG. 13 are compared to each other. That is, with the process conditions 2 in which the FA is used in the second preprocessing, both the correlation coefficient R and the expected standard error SEP are slightly improved and the calibration accuracy is improved, compared to the process conditions 1 in which the PCA is used. This effect can also be recognized substantially in the same manner from the comparison between the process conditions 4 and the process conditions 7. However, in FIG. 13, the effect of the usage of the FA in the second preprocessing is slightly less than the effect of the usage of the PNS in the first preprocessing. The reason thereof is assumed to be that the FA is effective mainly in decreasing the effect of the random noise and the random noise is slightly included in the measurement data used in the analysis of FIG. 13.

Effect of Usage of $\beta$ Divergence as Independence Index of ICA

An effect of usage of the $\beta$ divergence as the independence index of the ICA can be recognized, when the process conditions 1 and the process conditions 4 of FIG. 13 are compared to each other. That is, with the process conditions 4 in which the $\beta$ divergence is used as the independence index of the ICA, both the correlation coefficient R and the expected standard error SEP are slightly improved and the calibration accuracy is improved, compared to the process conditions 1 in which the kurtosis is used. This effect can also be recognized substantially in the same manner from the comparison between the process conditions 6 and the process conditions 8. However, in FIG. 13, the effect of the usage the $\beta$ divergence as the independence index of the ICA is slight, and in comparison between the process conditions 2 and the process conditions 7, the calibration accuracy is slightly degraded in a case where the $\beta$ divergence is used. The reason thereof is assumed to be that the $\beta$ divergence is effective mainly in decreasing the effect of the outlier such as the spike noise, and the spike noise is slightly included in the measurement data used in the analysis of FIG. 13.

C-5. Evaluation of Effects of Algorithms on Calibration Accuracy (2)

FIG. 14A to FIG. 14H are diagrams showing results obtained by evaluating the effects of various algorithms when various variations exist, and FIG. 15 is a diagram showing collection of the calibration accuracy of FIG. 14A to FIG. 14H. In the effects evaluation, 40 types of sample voice signals obtained by mixing two voice items v1 and v2 at random ratios, are created as the data to be processed, and the calibration curves are created in accordance with the procedures of FIG. 5 and FIG. 8. The calibration target is a ratio of the first voice v1. A reason for setting the voice signals as the data to be processed, is for checking the effect of various algorithms with respect to the data to be processed including various variations.

FIG. 14A to FIG. 14H each show a relationship between a calibration value obtained when using the calibration curve obtained as described above, and an actual value. The following three types of variations are added to the sample voice signals. (1) Gaussian noise: Gaussian noise having dispersion of 0.05 is added. (2) Spike noise: Spike noise according to $\chi^2$ distribution of a parameter 5 is added at a ratio of 1%. (3) Baseline variation: the constant baseline variation E, the variations linearly dependent on a wavelength, and the variation $\lambda^2$ secondarily dependent on a wavelength are randomly added in order of $10^{-1}$, $10^{-5}$, and $10^{-6}$.

Eight types of process conditions of FIG. 15 are the same as those shown in FIG. 13. The SNV is disclosed in brackets in FIG. 15 because the sample voice signals may be considered as signals subjected to the SNV, as those are previously created as normalized signals in which an average value is 0 and a standard deviation is 1.

Effect of Usage of Project on Null Space (PNS) in First Preprocessing

An effect of usage of the PNS in the first preprocessing is slight in comparison between the process conditions 1 and the process conditions 3 of FIG. 15, but is considerably large in comparison between the process conditions 2 and the process conditions 6. The considerably large effect of the PNS can also be recognized, in comparison between the process conditions 4 and the process conditions 5, and comparison between the process conditions 7 and the process conditions 8. That is, the effect of usage of the PNS in the first preprocessing becomes more significant, when employing at least one of usage of the FA in the second preprocessing, and usage of β divergence as the independence index of the ICA.

Effect of Usage of Factor Analysis (FA) in Second Preprocessing

An effect of usage of the FA in the second preprocessing is considerably large so as to be recognized from comparison between the process conditions 1 and the process conditions 2 of FIG. 15, and the considerably large effect thereof can also be recognized, in the same manner, from comparison between the process conditions 3 and the process conditions 6, comparison between the process conditions 4 and the process conditions 7, and comparison between the process conditions 5 and the process conditions 8. In addition, the effect of usage of the FA in the second preprocessing becomes more significant, when employing at least one of usage of the PNS in the first preprocessing, and usage of β divergence as the independence index of the ICA.

Effect of Usage of β Divergence as Independence Index of ICA

An effect of usage of the β divergence as the independence index of the ICA is slight in comparison between the process conditions 1 and the process conditions 4 of FIG. 15, but is considerably large in comparison between the process conditions 3 and the process conditions 5, and the considerably large effect thereof is also obtained, in the same manner, from comparison between the process conditions 2 and the process conditions 7 or comparison between the process conditions 6 and the process conditions 8. That is, the effect of usage of the β divergence as the independence index of the ICA becomes more significant, when employing at least one of usage of the PNS in the first preprocessing, and usage of the FA in the second preprocessing.

As recognized from the evaluation result of FIG. 15 described above, the effect of usage of the PNS in the first preprocessing, the effect of usage of the FA in the second preprocessing, and the effect of usage of the β divergence as the independence index of the ICA are more significant, in a case where the data in which various variations exist is set as the data to be processed.

C-6. Evaluation of Effects of Algorithms on Calibration Accuracy (3)

FIG. 16A to FIG. 16F are diagrams showing results obtained by evaluating the effects of various algorithms when only one type of variation exists from three types of variations such as Gaussian noise, the baseline variation, and the spike noise, and FIG. 17 is a diagram showing collection of the calibration accuracy of FIG. 16A to FIG. 16F. In the effects evaluation, in the same manner as FIG. 15, 40 types of sample voice signals obtained by mixing two voice items v1 and v2 at random ratios, are created as the data to be processed, and the calibration curves are created in accordance with the procedures of FIG. 5 and FIG. 8. However, only one type of variation among the three types of variations such as the Gaussian noise, the baseline variation, and the spike noise, is added to the sample voice signals.

As shown in FIG. 17, the data to which the Gaussian noise is added is subjected to the process with the process conditions 1 and the process conditions 2. The process conditions 1 and the process conditions 2 are different from each other in a point of using the PCA or using FA as the second preprocessing. If the FA is used as the second preprocessing for the data to which the Gaussian noise is added, the calibration accuracy is significantly improved compared to the case of using the PCA. From this comparison, it is confirmed that the FA is effective in decreasing the effect of the random noise such as the Gaussian noise.

As shown in FIG. 17, the data to which the baseline variation is added is subjected to the process with the process conditions 1 and the process conditions 3. The process conditions 1 and the process conditions 3 are different from each other in a point of using the SNV or using PNS as the first preprocessing. If the PNS is used as the first preprocessing for the data to which the baseline variation is added, the calibration accuracy is significantly improved compared to the case of using only the SNV. From this comparison, it is confirmed that the PNS is effective in decreasing the effect of the baseline variation.

As shown in FIG. 17, the data to which the spike noise is added is subjected to the process with the process conditions 1 and the process conditions 4. The process conditions 1 and the process conditions 4 are different from each other in a point of using the kurtosis or using β divergence as the independence index of the ICA. If the β divergence is used as the independence index of the ICA for the data to which the spike noise is added, the calibration accuracy is significantly improved compared to the case of using the kurtosis. From this comparison, it is confirmed that the β divergence is effective in decreasing the effect of the spike noise.

D. EFFECT OF ROBUST REGRESSION METHOD ON CALIBRATION ACCURACY

Figure 18:
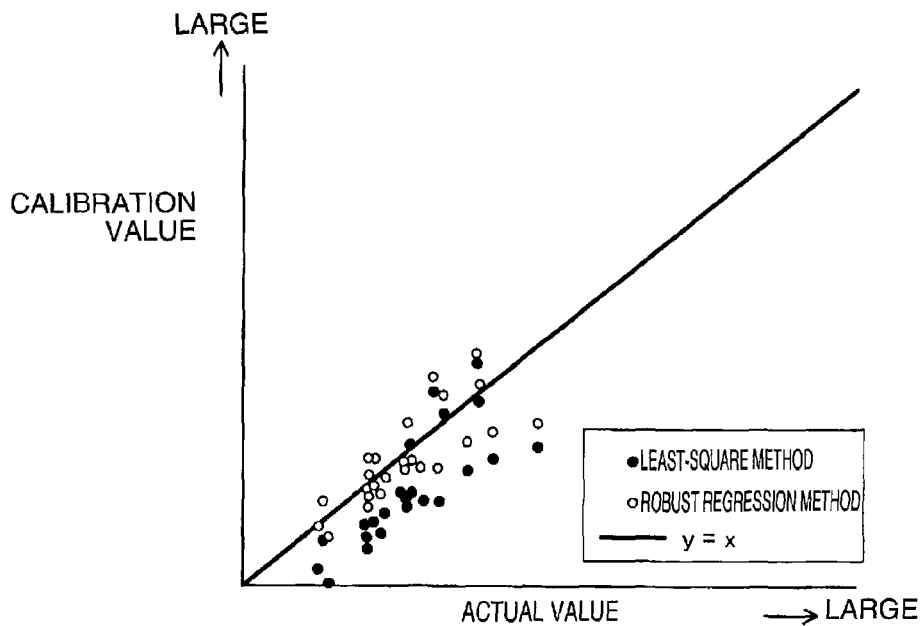
FIG. 18 is a graph showing comparison of calibration accuracy expected with a calibration curve obtained using a robust regression method and a calibration curve obtained using a least-squares method.

FIG. 18 is a graph showing comparison of the calibration accuracy expected with a calibration curve obtained using the robust regression method and the calibration curve obtained using the least-squares method. Herein, light including near infrared light is emitted to vegetables, the spectrum of the spectral reflectance obtained from the diffusely-reflected light thereof is measured with the spectroscopic measurement instrument to acquire the data to be processed, and the calibration curve is created according to the procedures of FIG. 5 and FIG. 8. A reason for converting the spectrum of the spectral reflectance obtained from the diffusely-reflected light from the human body into the data to be processed, is for checking the effect of the robust regression method with respect to the data to be processed including various variations. The step of acquiring the regression equation of the calibration curve which is Step S210 of FIG. 8 includes the case of using the robust regression method and the case of using the least-squares method. As the calibration result with respect to test data, results expected to be obtained with both a calibration curve obtained using the robust regression method (hereinafter, referred to as a "calibration curve of the embodiment") and a calibration curve obtained using the least-squares method (hereinafter, referred to as a "calibration curve of the reference example") are plotted in the graph of FIG. 18. O represents the case of using the calibration curve of the embodiment and • represents the case of using the calibration curve of the reference example. As is clear from the graph, in the calibration result obtained by using the calibration curve of the embodiment, a linear line is close to y=x, that is, the actual values and the calibration values coincide with each other, compared to the calibration result obtained by using the calibration curve of the reference example. In practice, the expected standard error SEP between the actual value and the calibration value of the test data is 35.74 in the calibration curve of the reference example and 21.52 in the calibration curve of the embodiment, and therefore the calibration result obtained by using the calibration curve of the embodiment has a significantly smaller error than the calibration result obtained by using the calibration curve of the reference example.

E. REASON FOR EMPLOYING ROBUST REGRESSION METHOD

As a quantitative component analysis method of the related art, multiple regression analysis, principal component regression analysis (PCR), and PLS regression analysis are generally known. In the analysis methods of the related art, in order to create a regression line for quantitating, first, measurement data is separated into the smallest number (at least smaller than a number of dimensions of the data) of component signals (basis vectors) for approximating the measurement data, and the regression equation for approximating the actual value is created by using the component signals. More specifically, in the principal component regression analysis, the following process is performed, for example.

Figure 19:
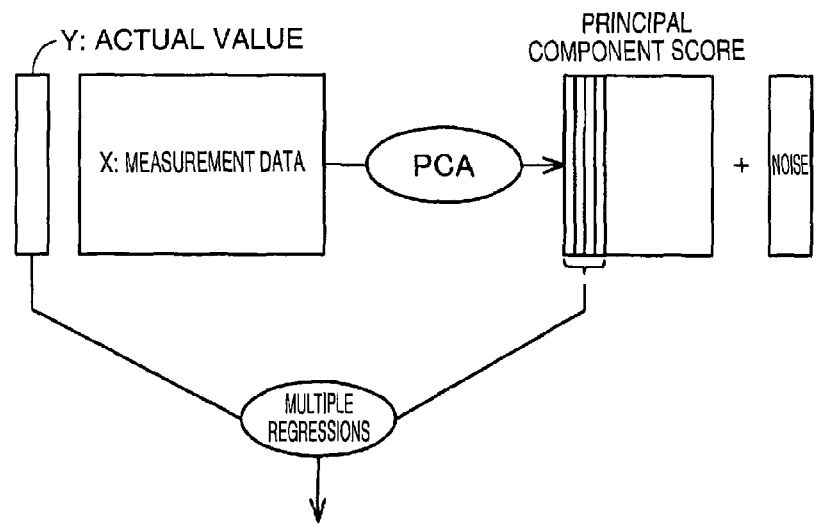
FIG. 19 is an explanatory diagram showing a principal component regression analysis method.

FIG. 19 is an explanatory diagram showing the principal component regression analysis method. As shown in the drawing, first, the principal components analysis (PCA) is performed with respect to the measurement data X. Next, an equation for approximating the actual value Y is acquired by multiple regression, using only a principal component score having a large contribution ratio among principal component scores obtained by the PCA. The acquired approximation equation is given in a formula (a) of the drawing. In a case of acquiring a regression coefficient q so as to have a minimum square error, an analytically-solved formula (b) of the drawing can be acquired. With respect to this, in a case of acquiring the approximation equation using the robust regression method, it is necessary to perform optimization provided with constrained conditions other than the square error, for determining the regression coefficient q. In addition, the constrained conditions are generally undefined, and disturbance of other components due to the usage of the multiple regressions is also considered. Accordingly, it is difficult to perform the analysis methods of the related art for improving only the robust property with respect to the target component amount included in the measurement data X by robust regression.

Meanwhile, in the quantitative component analysis technology using the independent component of the embodiment, from a viewpoint of the property of the independent component, each independent component directly corresponds to some components included in the measurement data, and the entire information of the target component is concentrated to the independent component corresponding to the target component. Accordingly, it is not necessary to mix unnecessary component by purposely to the components using the multiple regressions as in the analysis method of the related art, and the regression equation can be created by single regression using the mixing coefficient of one independent component corresponding to the target component. If the single regression is used, since the regression line itself has a one-to-one relationship between one independent component and the actual value, in a case of performing robust regression between the mixing coefficient of the independent component and the actual value, even when the outlier exists, for example, it is possible to reliably create the regression equation with respect to the target component with a significantly-suppressed effect of the outlier. As a result, it is possible to significantly improve the accuracy of the calibration value itself to be estimated by the regression equation. Further, when performing the independent component analysis, the reduced effect of the outlier or noise can be reflected in the calibration curve itself using the β divergence.

F. MODIFICATION EXAMPLES

The invention is not limited to the embodiments described above or other modification examples, and can be executed in various embodiments within a range not departing from a gist thereof, and the following modifications can also be performed, for example.

Modification Example 1

In the embodiments described above, the test object observation data acquisition unit 510 (FIG. 10) acquires the calibrating data set DS2 from the hard disk drive 30 to acquire the independent component matrix Y including the independent component corresponding to the target component, and the mixing coefficient calculation unit 530 (FIG.

10) acquires the estimated mixing matrix ^A of the test object based on the absorbance spectrum of the test object and the independent component matrix Y and extracts the k-th row mixing coefficient $\alpha_k$ corresponding to the target component order k from the estimated mixing matrix ^A, to acquire the mixing coefficient of the target component for the test object, but the invention is not limited thereto. For example, the modification example may have a configuration of performing the following parts (i) and (ii) in order.

(i) The calibrating data set DS2 stored in the hard disk drive 30 is read out to acquire the k-th row element (independent component) $Y_k$ corresponding to the target component order k from the independent component matrix Y included in the calibrating data set DS2. The independent component $Y_k$ has a highest correlation with respect to the chlorophyll amount and corresponds to the chlorophyll amount. (ii) Next, an inner product of the extracted independent component $Y_k$ and the spectrum $X_p$ of the test object which is the observation data (for example, normalized spectrum obtained in Step S320) is acquired, and an inner product value thereof is set as the mixing coefficient $\alpha_k$ of the target component. That is, an arithmetic operation according to the following formula (27) is performed.

$$\alpha_k = X_p \cdot Y_k \quad (27)$$

Herein, since it is assumed that the observation data is a linear sum of the independent components, and orthogonality between the independent components is sufficiently high, by calculating the inner product between the spectrum which is the observation data and the independent component matrix of the target component, only the value of the independent component remains and values of all of the other components become 0. Accordingly, the mixing coefficient $\alpha_k$ of the target component is easily calculated. However, in a case where the orthogonality between the independent components is not sufficiently high, it is preferable to acquire the estimated mixing matrix ^A of the formula (15) without using the arithmetic operation of the formula (27).

In the process of the part (i), the CPU 10 functions as the calibrating data acquisition unit. In the process of the part (ii), the CPU 10 functions as the mixing coefficient calculation unit. In addition, instead of the configuration of the part (i), the calibrating data acquisition unit may be configured to acquire the independent component $Y_k$ from a storage unit such as the hard disk drive 30 in which the k-th row element (independent component) $Y_k$ corresponding to the target component order k from the independent component matrix Y is previously stored. In a case of using the inner product, the independent component corresponding to the target component is only necessary, and therefore the other independent components are not necessary. In this case, the independent component is the vector, and it is not necessary to store the target component order.

Modification Example 2

In the embodiments and the modification example described above, it is configured to detect the chlorophyll amount by setting the green vegetables as the test object, but instead of the chlorophyll amount of the green vegetables, the invention can be applied to various test objects and target components such as oleic acid of meat, collagen of skin of a person, glucose amount of a living body of a person, and the like. That is, the invention can be applied to various test objects and target components as long as the calibration curve can be created by preparing the samples configured with the same components as the test object. In the embodiments and the modification example, it is configured that the calibration is performed using the absorbance spectrum as the observation data, but a magnitude of voice from a specific voice source can be used for calibration with the same configuration, although the observation data is set as voice data in which voice items from a plurality of voice sources are mixed with each other, instead of the absorbance spectrum. That is, the invention can be applied to various observation data items as long as it is a signal including a sufficient amount of information for recognizing a statistical property of the signal source.

Modification Example 3

In the embodiments and the modification examples described above, the mixing coefficient estimation step has a configuration of acquiring the independent component matrix, acquiring the estimated mixing matrix, and extracting the mixing coefficient corresponding to the target component from the estimated mixing matrix, but it is not necessary to have this configuration. That is, any configuration can be used, as long as it is the configuration in which each independent component included in the observation data of each sample when separating the observation data into the plurality of the independent components is assumed, and the mixing coefficient corresponding to the target component is acquired for each sample, based on each independent component.

Modification Example 4

In the calibration curve creating method of the embodiments and the modification examples described above, it is configured to measure the content of the target component of the sample, but instead of this, the sample with known content of the target component may be prepared and the content may be input from a keyboard or the like.

Modification Example 5

In the embodiments and the modification examples described above, the number of elements m of the spectra S of the unknown component is empirically and experimentally determined in advance, but the number of elements m of the spectra S of the unknown component may be determined by minimum description length (MDL) or information criteria known as Akaike information criteria (AIC). In a case of using the MDL or the like, the number of elements m of the spectra S of the unknown component can be automatically determined by the arithmetic operation from the observation data of the sample. The MDL is, for example, described in "Independent component analysis for noisy data—MEG data analysis, 2000".

Modification Example 6

In the embodiments and the modification examples described above, the test object which is a target of the calibration process is configured with the same component as the sample used when creating the calibration curve, but in a case of acquiring the mixing coefficient using the inner product as in Modification Example 1, unknown components other than the same component as in the sample used when creating the calibration curve may be included in the test object. This is because, since the inner products between the independent components are assumed to be 0, the inner products between the independent components corresponding to the unknown components are also considered to be 0, and the effect of the unknown components can be ignored in a case of acquiring the mixing coefficient with the inner product.

Modification Example 7

For the computer used in the embodiments and the modification examples described above, an exclusive apparatus can be used instead of the personal computer. For example, the personal computer which implements the calibrating method of the target component can be set as an exclusive calibration apparatus.

Modification Example 8

In the embodiments described above, the input of the spectrum of spectral reflectance of the sample or the test object is performed by inputting the spectrum measured by the spectroscopic measurement instrument, but the invention is not limited thereto. For example, the optical spectrum may be estimated from a plurality of band images having different wavelength bands and the optical spectrum may be input. The band images are obtained, for example, by imaging the sample or the test object with a multiband camera including a filter capable of changing transmission wavelength bands.

Modification Example 9

In the embodiments and the modification examples described above, the functions implemented by the software may be implemented by the hardware.

Among the configuration elements of the embodiments and the modification examples described above, the elements other than the elements disclosed in independent claims are additional elements and may be suitably omitted.

What is claimed is:

1. A method of calibrating a spectroscopic measurement instrument using a single test object, comprising:
    (a) acquiring, via software executing on a computer, observation data of a plurality of samples of the single test object from the spectroscopic measurement instrument;
    (b) acquiring, via software executing on the computer, content of a target component of each sample;
    (c) estimating, via software executing on the computer, a plurality of independent components when the observation data of each sample is separated into the plurality of independent components, and acquiring a mixing coefficient corresponding to the target component for each sample, based on the plurality of independent components;
    (d) acquiring, via software executing on the computer, a regression equation of a calibration curve based on the content of the target component of the plurality of samples and the mixing coefficient for each sample; and
    (e) calibrating the spectroscopic measurement instrument using the calibration curve,
    wherein (c) includes:
        (i) acquiring, via software executing on the computer, an independent component matrix including the independent component of each sample,
        (ii) acquiring, via software executing on the computer, an estimated mixing matrix showing a vector set for regulating a ratio of an independent component element of each independent component in each sample, from the independent component matrix, and
        (iii) acquiring, via software executing on the computer, a correlation of content of the target component of the plurality of samples, for each vector included in the estimated mixing matrix, and to select the vector which is determined to have a highest correlation, as a mixing coefficient corresponding to the target component,
    in (i), the computer acquires the independent component matrix by performing a first preprocessing including normalization of the observation data, a second preprocessing including whitening, and an independent component analysis process in this order,
    the computer uses $\beta$ divergence as an independence index of the independent component analysis process, and
    a robust regression method is used in (d) acquiring the regression equation of the calibration curve.

2. The method according to claim 1,
    wherein the computer performs whitening by factor analysis in the second preprocessing.

3. An apparatus for calibrating a spectroscopic measurement instrument using a single test object, comprising:
    an input interface configured to connect to the spectroscopic measurement instrument; and
    a processor configured to:
        acquire observation data of a plurality of samples of the single test object via the input interface;
        acquire content of a target component of each sample;
        estimate a plurality of independent components when the observation data of each sample is separated into the plurality of independent components, and acquire a mixing coefficient corresponding to the target component for each sample, based on the plurality of independent components; and
        acquire a regression equation of the calibration curve based on the content of the target component of the plurality of samples and the mixing coefficient for each sample,
    wherein the processor estimates of the plurality of independent components and acquires of the mixing coefficient by:
        acquiring an independent component matrix including each independent component of each sample,
        acquiring an estimated mixing matrix showing a vector set for regulating a ratio of an independent component element of each independent component in each sample, from the independent component matrix, and
        acquiring a correlation of content of the target component of the plurality of samples, for each vector included in the estimated mixing matrix, and selecting the vector which is determined to have a highest correlation, as a mixing coefficient corresponding to the target component,
    the processor acquires the independent component matrix by performing a first preprocessing including normalization of the observation data, a second preprocessing including whitening, and an independent component analysis process in this order,
    the processor uses $\beta$ divergence as an independence index of the independent component analysis process, and
    the processor uses a robust regression method.

4. The apparatus according to claim 3,
wherein the processor performs normalization after a process performed by project on null space in the first preprocessing.

5. The apparatus according to claim 3,
wherein the processor performs whitening by factor analysis in the second preprocessing.

6. The apparatus according to claim 3, further comprising:
a storage medium which stores the independent component matrix calculated by the processor, a target component order which shows a position of the mixing coefficient selected by the processor in the estimated mixing matrix, and the regression equation calculated by the processor.

7. A method of calibrating a spectroscopic measurement instrument using a single test object, comprising:
  (a) acquiring, via software executing on a computer, observation data of a plurality of samples of the single test object from the spectroscopic measurement instrument;
  (b) acquiring, via software executing on the computer, content of a target component of each sample;
  (c) estimating, via software executing on the computer, a plurality of independent components when the observation data of each sample is separated into the plurality of independent components, and acquiring a mixing coefficient corresponding to the target component for each sample, based on the plurality of independent components;
  (d) acquiring, via software executing on the computer, a regression equation of a calibration curve based on the content of the target component of the plurality of samples and the mixing coefficient for each sample; and
  (e) calibrating the spectroscopic measurement instrument using the calibration curve,
wherein (c) includes:
  (i) acquiring, via software executing on the computer, an independent component matrix including the independent component of each sample,
  (ii) acquiring, via software executing on the computer, an estimated mixing matrix showing a vector set for regulating a ratio of an independent component element of each independent component in each sample, from the independent component matrix, and
  (iii) acquiring, via software executing on the computer, a correlation of content of the target component of the plurality of samples, for each vector included in the estimated mixing matrix, and to select the vector which is determined to have a highest correlation, as a mixing coefficient corresponding to the target component,
in (i), the computer acquires the independent component matrix by performing a first preprocessing including a process performed by project on null space and thereafter normalization of the observation data, a second preprocessing including whitening, and an independent component analysis process in this order,
the computer uses $\beta$ divergence as an independence index of the independent component analysis process, and
a robust regression method is used in (d) acquiring the regression equation of the calibration curve.

8. The method according to claim 7,
wherein the computer performs whitening by factor analysis in the second preprocessing.

* * * * *